United States Patent
Chong

(10) Patent No.: US 9,446,995 B2
(45) Date of Patent: Sep. 20, 2016

(54) SYNTHESIS OF THERAPEUTIC AND DIAGNOSTIC DRUGS CENTERED ON REGIOSELECTIVE AND STEREOSELECTIVE RING OPENING OF AZIRIDINIUM IONS

(71) Applicant: Hyun-Soon Chong, Chicago, IL (US)

(72) Inventor: Hyun-Soon Chong, Chicago, IL (US)

(73) Assignee: Illinois Institute of Technology, Chicago, IL (US)

( * ) Notice: Subject to any disclaimer, the term of this patent is extended or adjusted under 35 U.S.C. 154(b) by 7 days.

(21) Appl. No.: 13/896,524

(22) Filed: May 17, 2013

(65) Prior Publication Data

US 2013/0310555 A1    Nov. 21, 2013

Related U.S. Application Data

(60) Provisional application No. 61/649,437, filed on May 21, 2012.

(51) Int. Cl.

| C07C 253/14 | (2006.01) |
|---|---|
| C07C 209/08 | (2006.01) |
| C07C 209/74 | (2006.01) |
| C07C 213/00 | (2006.01) |
| C07C 209/10 | (2006.01) |
| C07C 319/04 | (2006.01) |
| C07C 247/10 | (2006.01) |
| C07C 327/06 | (2006.01) |
| C07D 221/10 | (2006.01) |
| C07B 43/00 | (2006.01) |
| C07B 43/04 | (2006.01) |
| C07C 331/28 | (2006.01) |
| C07C 227/18 | (2006.01) |
| C07D 255/02 | (2006.01) |
| C07D 217/04 | (2006.01) |
| C07D 209/16 | (2006.01) |
| C07C 209/62 | (2006.01) |
| C07D 265/32 | (2006.01) |
| C07D 207/404 | (2006.01) |

(52) U.S. Cl.
CPC .............. C07B 43/04 (2013.01); C07B 43/00 (2013.01); C07C 209/08 (2013.01); C07C 209/10 (2013.01); C07C 209/62 (2013.01); C07C 209/74 (2013.01); C07C 213/00 (2013.01); C07C 227/18 (2013.01); C07C 247/10 (2013.01); C07C 253/14 (2013.01); C07C 319/04 (2013.01); C07C 327/06 (2013.01); C07C 331/28 (2013.01); C07D 207/404 (2013.01); C07D 209/16 (2013.01); C07D 217/04 (2013.01); C07D 221/10 (2013.01); C07D 255/02 (2013.01); C07D 265/32 (2013.01); C07B 2200/07 (2013.01); C07C 2102/08 (2013.01)

(58) Field of Classification Search
CPC ... C07B 43/04; C07B 43/00; C07B 2200/07; C07C 331/28; C07C 227/18; C07C 209/62; C07C 209/08; C07C 209/10; C07C 327/06; C07C 209/74; C07C 247/10; C07C 319/04; C07C 213/00; C07C 253/14; C07C 2102/08; C07D 255/02; C07D 217/04; C07D 221/10; C07D 265/32; C07D 207/404; C07D 209/16
USPC ......... 562/437, 433; 546/150, 143; 549/149; 548/546, 504; 564/455, 487; 563/433; 544/171; 558/18
See application file for complete search history.

(56) References Cited

U.S. PATENT DOCUMENTS

| 4,831,175 | A | 5/1989 | Gansow et al. |
|---|---|---|---|
| 5,847,216 | A | 12/1998 | Ott-Dembrowski et al. |
| 6,207,858 | B1 | 3/2001 | Chinn et al. |
| 6,252,076 | B1 * | 6/2001 | Hong et al. ............ 544/321 |
| 6,875,866 | B2 | 4/2005 | Dahanukar et al. |
| 7,081,452 | B2 | 7/2006 | Brechbiel et al. |
| 7,163,935 | B2 | 1/2007 | Brechbiel et al. |
| 7,368,100 | B2 | 5/2008 | Brechbiel et al. |
| 7,563,433 | B2 | 7/2009 | McBride et al. |
| 7,597,876 | B2 | 10/2009 | McBride et al. |
| 7,799,934 | B2 | 9/2010 | Antilla et al. |
| 7,993,626 | B2 | 8/2011 | McBride et al. |
| 8,153,101 | B2 | 4/2012 | McBride et al. |
| 2003/0108486 | A1 | 6/2003 | Platzek et al. |
| 2009/0155166 | A1 | 6/2009 | McBride et al. |
| 2009/0162290 | A1 | 6/2009 | Benes et al. |
| 2010/0322855 | A1 | 12/2010 | Chong |
| 2011/0110854 | A1 | 5/2011 | McBride et al. |

FOREIGN PATENT DOCUMENTS

| DE | 36 25 417 C2 | 10/1998 |
|---|---|---|
| DE | 198 49 465 A1 | 4/2000 |
| DE | 103 05 463 A1 | 8/2004 |
| WO | WO 2010/011367 A2 | 1/2010 |

OTHER PUBLICATIONS

Metro, T-X., Highly Enantioselective Synthesis of Linear b-Amino Alcohols, 2009 Chem. Eur. J. 15: 1064-1070.*
Metro, T-X.,Rearrangement of b-amino alcohols via aziridiniums: a review, 2010 Chem. Soc. Rev. 39: 89-102.*
Chandrasekhar, S.,"Unexpected formation of 3-substituted 1, 2, 3, 4-tetrahydroisoquinolines during tosylation of N, N-dibenzylaminols." 1999 Organic Letters 1.6 : 877-878.*

(Continued)

*Primary Examiner* — Samantha Shterengarts
*Assistant Examiner* — Matt Mauro
(74) *Attorney, Agent, or Firm* — Pauley Erickson & Rottis

(57) ABSTRACT

Stereoselective and regioselective synthesis of compounds via nucleophilic ring opening reactions of aziridinium ions for use in stereoselective and regioselective synthesis of therapeutic and diagnostic compounds.

4 Claims, 11 Drawing Sheets

(56) References Cited

OTHER PUBLICATIONS

March, J., March's Advanced Organic Chemistry 2007, 6$^{th}$ Edition, Wiley Interscience, p. 1-2357.*

Hu, X. E.,"Nucleophilic ring opening of aziridines." Tetrahedron 60.12 (2004): 2701-2743.*

Gala, D., "Development of an efficient process for the preparation of sch 39166: Aziridinium chemistry on scale." Organic process research & development 8.5 (2004): 754-768.*

Pearson, R. G., "Hard and soft acids and bases." Journal of the American Chemical Society 85.22 (1963): 3533-3539.*

Hyun-Soon Chong et al., "Novel synthetic ligands for targeted PET imaging and radiotherapy of copper," Bioorganic & Medical Chemistry Letters, Sep. 2007, vol. 17, No. 22, pp. 6107-6110.

Noah Birch et al., "Expert Opinion—Iron chelators as therapeutic iron depletion agents," Expert Opin. Ther. Patents, 2006, vol. 16, No. 11, pp. 1533-1556.

Hyun-Soon Chong et al., "A novel cholic acid-based contrast enhancement agent for targeted MRI," Bioorganic & Medicinal Chemistry Letters, Jan. 18, 2008, pp. 2505-2508.

Cacheris, W.P. et al., "Thermodynamic Study of Lanthanide Complexes of 1,4,7-Triazacyclononane . . . ," Inorg. Chem, 1987, 26, pp. 958-960.

\* cited by examiner

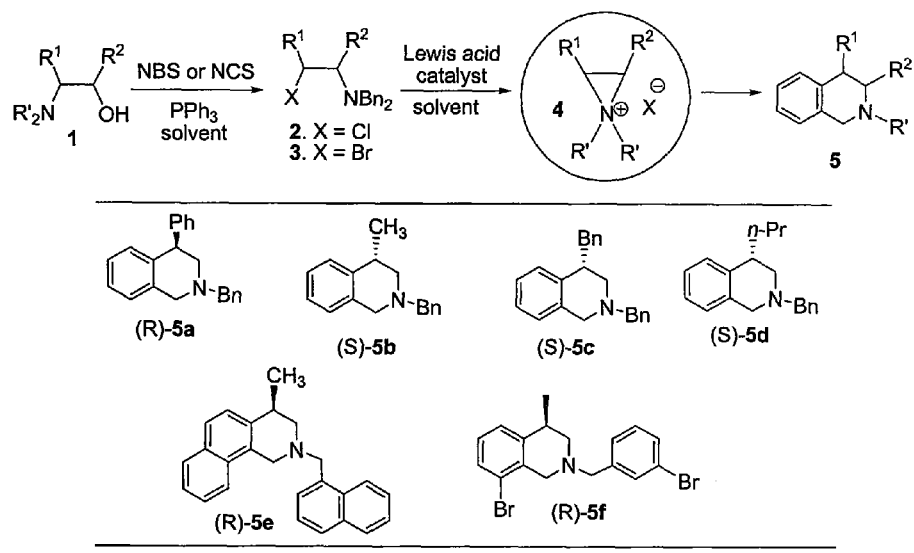

| $R^1/R^2/R'$ | X | Solvent/Temp | Lewis catalyst | Product | Yield(%)/ee(%) |
|---|---|---|---|---|---|
| (R)-Ph/H/Bn | Cl | toluene/0°C | $AlCl_3$ | (R)-5a | 73/73 |
| (R)-Ph/H/Bn | Br | toluene/0°C | $AlCl_3$ | (R)-5a | 81/76 |
| (R)-Ph/H/Bn | Br | DCE/0 °C | $AlCl_3$ | (R)-5a | 92/81 |
| (R)-Ph/H/Bn | Br | toluene/0 °C | $TiCl_4$ | (R)-5a | 74/75 |
| (R)-Ph/H/Bn | Br | toluene/0 °C | $InCl_3$ | (R)-5a | 87/62 |
| (S)-$CH_3$/H/Bn | Br | toluene/reflux | $AlCl_3$ | (S)-5b | 90/100 |
| (R)-Bn/H/Bn | Br | toluene/reflux | $AlCl_3$ | (S)-5c | 98/90 |
| (S)-Pr/H/Bn | Br | toluene/reflux | $AlCl_3$ | (S)-5d | 62/100 |
| (R)-$CH_3$/H/Naphthyl | Br | toluene/reflux | $AlCl_3$ | (R)-5e | 49/100 |
| (S)-$CH_3$/H/m-Bn-Br | Br | toluene/0 °C | $AlCl_3$ | (R)-5f | 73/85 |

Fig. 5

| Substrate | R¹ | R² | R³ | R' | Product | Yield (%) |
|---|---|---|---|---|---|---|
| (R)-3b | CH₃ | Bn | Bn | allyl | (S)-4a | 44 |
| (R)-3b | CH₃ | Bn | Bn | vinyl | (S)-4b | 51 |
| (R)-3b | CH₃ | Bn | Bn | Me | (S)-4c | 33 |
| (S)-3a | Ph | Bn | Bn | allyl | (R)-5d | 31 |
| (S)-3d | iPr | Bn | Bn | allyl | (R)-4e | 41 |
| (R)-3c | Bn | Bn | Bn | allyl | (S)-4f | 44 |

| Substrate | R | X | Reaction time | Product (Yield) |
|---|---|---|---|---|
| (R)-3a | Ph | Br | 3 m | (R)-5a (100%) |
| (S)-3a | Ph | Br | 3 m | (S)-5a (100%) |
| (S)-3b | CH₂SBn | Br | 6 h | (S)-5b (100%) |
| (R)-2c | Chx | I | 1.5 h | (S)-5c (100%) |

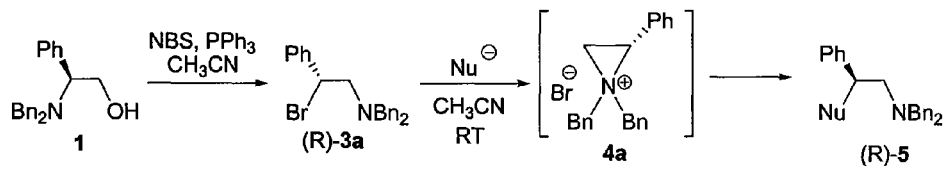
| Nu/reagent | Time | Product (Yield) |
| --- | --- | --- |
| NaCN | 1 min | (R)-5a (96%) |
| NaN$_3$ | 5 min | (R)-5b (96%) |
| TBAF | 1 min | (R)-5c (100%) |
| NH$_4$OH | 1 min | (R)-5d (95%) |
| 1M NaOH | 10 min | (R)-5e (90%) |
| H$_2$O | 10 min | (R)-5e (93%) |
| H$_2$O/AgCN | 1 min | (R)-5e (100%) |
| 1-propanethiol | 3.5 h | (R)-5f (96%) |
| Bn$_2$NH | 1 h | (R)-5g (91%) |
| TFA/DIPEA | 7 h | (R)-5h (85%) |
| Imidazole | 20 min | (R)-5i (76%) |
| KNPhth | 50 min | (R)-5j (100%) |
| CH$_3$COSH/DIPEA | 1 min | (R)-5k (93%) |
| PhNH$_2$ | 10 min | (R)-5l (88%) |
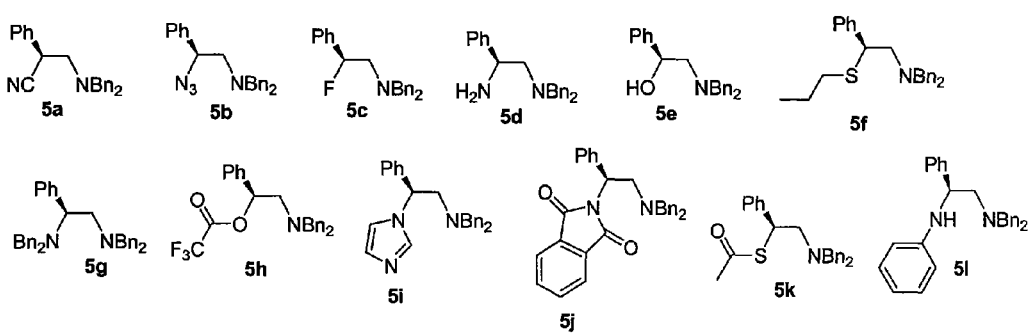
Fig. 15

SYNTHESIS OF THERAPEUTIC AND DIAGNOSTIC DRUGS CENTERED ON REGIOSELECTIVE AND STEREOSELECTIVE RING OPENING OF AZIRIDINIUM IONS

CROSS REFERENCE TO RELATED APPLICATION

This application claims the benefit of U.S. Provisional Patent Application, Ser. No. 61/649,437, filed on 21 May 2012. The Provisional Patent Application is hereby incorporated by reference herein in its entirety and is made a part hereof, including but not limited to those portions which specifically appear hereinafter.

This invention was made with government support under Grant Numbers NIHCA112503 awarded by the National Institutes of Health. The U.S. government has certain rights in this invention.

FIELD OF THE INVENTION

This invention relates generally to stereoselective and regioselective synthesis of compounds and, more particularly, to nucleophilic ring opening reactions of aziridinium ions for use in stereoselective and regioselective synthesis of compounds.

BACKGROUND OF THE INVENTION

Aziridinium ions have been utilized as reactive intermediates in asymmetric synthesis of pharmaceuticals, and other complex natural products. In addition, aziridinium ions are involved in anticancer activity of nitrogen mustards and anticancer drugs such as chlorambucil (CMB), mechlorethamine, and phosphamide mustard. The reaction of aziridinium ion intermediates derived from the mustards with guanine residues in DNA to form interstrand cross-link has been found to produce the biological activity. Although aziridinium ions possess great potential as building blocks for preparation of biologically active molecules, the reactivity and synthetic applications of aziridinium ions has not been systematically investigated. This is in part due to difficulties in isolation and characterization of the strained three-membered rings and the lack of general and efficient methods for synthesis of optically active aziridinium ions with functionalities. Aziridinium salts are amphiphilic species that can possess both nucleophilic and electrophilic components. The electrophilic carbons in the aziridinium salts are expected to react with nucleophiles under mild conditions, and the nucelophilic N-substituents, C-substitutents, or counteranions in the salts can also attack the electrophilic carbon present in the aziridinium ion in intramolecular nucleophilic reactions. While the other three-membered aziridines and epoxides have numerous applications in organic synthesis of important drugs, applications of aziridinium ion chemistry to drug synthesis remains an under-explored area.

SUMMARY OF THE INVENTION

A general object of the invention is to provide for synthesis of chemical compounds, such as for use in medical diagnosis and/or treatment, via stereoselective and regioselective ring opening reactions of an aziridinium ion. The synthesis methods of this method can be used to provide new or existing drugs in shorter reaction steps and higher yields than conventional methods, and can reduce or eliminate complicated purification processes that have provided complications in large scale manufacturing. Exemplary drug compounds that can be provided by the method of this invention are useful in, for example, magnetic resonance imaging of cancers, radioimmunotherapy (RIT) of cancers, and therapeutics of Parkinson's disease (PD), depression, and neurodegenerative diseases.

The present invention is directed to a process for preparation of a nucleophilic addition product, the process comprising the formation of a substituted amino halide from a substituted amino alcohol and conversion of the amino halide to an aziridinium ion followed by their stereoselective and regioselective reaction with a nucleophile. Among aspects of the present invention is a process for highly efficient preparation of key precursor molecules for important pharmaceuticals in clinical and preclinical use including Phenibut, Tryptamine, Selegiline, and Zevalin. The present invention discloses synthesis of nucleophilic addition products with stereoselectivity and regioselectivity including, without limitation, 1,2- and 1,3-diamines, 3,4-diamino nitriles, 1,2-amino ethers, α-branched chiral amines, γ-amino butyric acids (GABAs), tetrahydroisoquinolines, oxomorpholines, DTPA and NETA analogues, and important pharmaceutical intermediates via the process comprising conversion of a substituted amino alcohol to a substituted amino halide or an aziridinium ion followed by stereoselective and/or regioselective nucelophilic reaction of an aziridinium ion.

An object of the invention can be attained, at least in part, through a method of stereoselectively or regioselectively reacting the aziridinium ion in a nucleophilic ring opening reaction to obtain a compound. In one embodiment, the method includes converting a substituted β amino alcohol to a substituted aziridinium ion selected from:

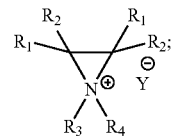

where: Y is a non-nucleophilic counter anion or a leaving group comprising halide, perchlorate, tetrafluoroborate, hexafluoroantimonate, mesylate, triflate, carbonate, nitrate, phthalimide, or succinimide; each of $R_{1-5}$ independently is or includes hydrogen, carboxyalkyl, alkylamido, alkyl, allyl, benzyl, benzyloxyalkyl, cycloalkyl, heterocyclyl, alkoxy, hydroxyalkyl, aryl, $CH_2Ar$, aryloxy, hydroxyaryl, heteroaryl, phenyl, vinyl, alkynyl, alkenyl, substituted carbonyl, halo, haloalkyl, nitrile, oxo, substituted oxo, substituted silyl, thiol, benzhydryl, silyl, substituted carboxyl, hydroxyalkyl, aminoalkyl, alkoxycarbonyl, alkylamido, furannylalkyl, alkylthioalkyl, arylhydroxyalkyl, indanyl, indolylalkyl, naphthylalkyl, imidazolylalkyl, pyridiylalkyl, phthalimidyl, maleimidyl, benzothiophenylalkyl, thiophenylalkyl, thioalkyl, thioaryl, thiobenzyl, hydroxy, hydroxyalkyl, aminoalkyl, tosyl, nosyl, a protected amine, carboxyl, carboxyalkyloxy, amino, carboxylic acid, holoalkylamido, aldehyde, alkylamino, amido, trityl, tert-butyloxycarbonyl, carbobenzyloxy, acetyl, dimethoxybenzyl, p-methoxybenzyl, an amide containing group, a thioamide containing group, an amino acid-containing group, an ester containing group, an amine protecting group; any two vicinal carbons of $R_1$ and $R_2$ together form a fused ring $—(CH_2)_n—$, $R_1$ and $R_2$ are bonded together and form a spiro ring, any of $R_{1-5}$ is or attached to chiral carbon, or two germinal carbons, or one of:

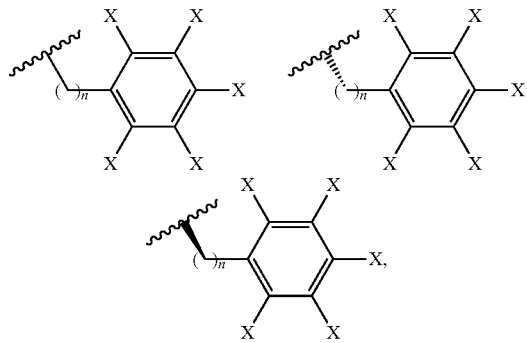

where n=1-10 and X is or includes hydrogen, halo, cyano, alkyl, aryl, hydroxyl, nitro, amino, alkylamino, dialkylamino, substituted amine, substituted carbonyl, isocyanate, cyanate ester, protected amine, protected hydroxyl, protected carboxyl, boronic acid, borinic acid, borinate ester, triflate, silyl, substituted silyl, thiocyano, isothiocyano, alkoxy, aryloxy, carboxyl, carboxylic acid, carboxyalkyl, carboxyalkyloxy, ester, amido, aldehydro, alkylamido, holoalkylamido, an ester containing group, an carbonyl containing group, a boron containing group, a tin containing group, an amide containing group, a thioamide containing group, or an amino acid-containing group, and $R_3$ can also be:

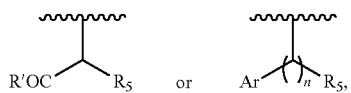

where Ar is an aromatic ring and n=1~3; R' independently is $OH$, $NH_2$, $NR''_2$, or $OR''$, wherein R'' independently is alkyl, tert-butyl, allyl, benzyl, $CH_2Ar$, silyl, trityl, an amine protecting group, a carboxyl protecting group, or a hydroxyl protecting group. The method further includes stereoselectively or regioselectively reacting the substituted aziridinium ion in a nucleophilic ring opening reaction to obtain the compound. Desirably, the stereoselectively or regioselectively reacting the aziridinium ion with a nucleophile to obtain the compound. The nucleophile can be an independent compound or part of or within the aziridinium ion, to provide an intramolecular reaction.

The aziridinium ion can be obtained by converting a substituted β amino alcohol to a substituted alkylating agent and converting the substituted alkylating agent to the substituted aziridinium ion. An exemplary substituted alkylating agent is a substituted β-amino halide is:

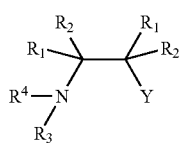

In embodiments of this invention, the reaction of aziridinium ion in the presence of a catalyst, such as a Lewis acid, an organocatalyst, or combinations thereof. In several embodiments, the reaction can proceed in situ, or in a "one-pot" reaction, such as without isolation of any intermediate compound, such as the aziridinium ion or any salt thereof.

References to substituent groups are to be generally understood in the common conventional meaning in the chemical arts. For example, the term "alkyl" means a straight-chain or branched alkyl substituent containing from, for example, about 1 to about 12 carbon atoms, preferably from about 1 to about 8 carbon atoms, more preferably from about 1 to about 6 carbon atoms. Examples of such substituents include methyl, ethyl, propyl, isopropyl, n-butyl, sec-butyl, isobutyl, tert-butyl, pentyl, isoamyl, hexyl, octyl, dodecanyl, and the like.

The term "cycloalkyl," as used herein, means a cyclic alkyl substituent containing from, for example, about 3 to about 30 carbon atoms, preferably from about 5 to about 14 carbon atoms, more preferably from about 5 to about 10 carbon atoms, and most preferably from about 5 to about 7 carbon atoms. Examples of such substituents include cyclopropyl, cyclobutyl, cyclopentyl, cyclohexyl, and the like.

The term "halo" or "halogen," as used herein, means a substituent selected from Group VIIA, such as, for example, fluorine, bromine, chlorine, and iodine. Preferably, the halo is bromine or iodine.

The term "aryl" refers to an unsubstituted or substituted aromatic carbocyclic substituent, as commonly understood in the art, and includes monocyclic and polycyclic aromatics such as, for example, phenyl, biphenyl, toluenyl, anisolyl, naphthyl, anthracenyl and the like. An aryl substituent generally contains from, for example, about 3 to about 30 carbon atoms, preferably from about 6 to about 18 carbon atoms, more preferably from about 6 to about 14 carbon atoms and most preferably from about 6 to about 10 carbon atoms. It is understood that the term aryl applies to cyclic substituents that are planar and comprise $4n+2\pi$ electrons, according to Hückel's Rule.

The term "heteroaryl" means a substituent defined by an aromatic heterocyclic ring, as is commonly understood in the art, including monocyclic and polycyclic heteroaryls containing from, for example, about 3 to about 30 carbon atoms, preferably from about 5 to about 10 carbon atoms, more preferably from about 5 to about 6 carbon atoms. Monocyclic heteroaryls include, for example, imidazolyl, thiazolyl, pyrazolyl, pyrrolyl, furanyl, pyrazolinyl, thiophenyl, oxazolyl, isoxazolyl, pyridinyl, pyridonyl, pyrimidinyl, pyrazinyl, and triazinyl substituents. Polycyclic heteroaryls include, for example, quinolinyl, isoquinolinyl, indolyl, purinyl, benzimidazolyl, benzopyrrolyl, and benzothiazolyl.

The term "alkoxy" embraces linear or branched alkyl groups that are attached to divalent oxygen. The alkyl group is the same as described herein. Examples of such substituents include methoxy, ethoxy, t-butoxy, and the like. The term "aryloxy" refers to substituents that have an aryl group attached to divalent oxygen. The aryl group is the same as described herein. An example of such substituents is phenoxy.

The term "alkylthio" as used herein, denotes a substituent with an alkyl group directly attached to a divalent sulfur atom. The alkyl group is the same as described herein. Examples of such substituents include methylthio, ethylthio, and the like. Similarly, the term "arylthio" as used herein, denotes a substituent with an aryl group directly attached to a divalent sulfur atom. The aryl group is the same as described herein.

The term "carboxyl" refers to the group —C(O)OH. The term "carboxyalkyl" refers to the group —RC(O)OH that is connected to the compound through the alkyl R group. The term "carboxyalkyloxy" refers to the group —ORC(O)OH, in which the R is an alkyl (e.g., $(CH_2)_n$ alkylene group, where n is 1 to 12) group.

The terms "amine" or "amino" as used herein are represented by the formula $NR^1R^2A^3$, where $R^1$, $R^2$, and $R^3$ can be, for example, independently, hydrogen or substituted or unsubstituted alkyl, cycloalkyl, alkenyl, cycloalkenyl, alkynyl, cycloalkynyl, aryl, or heteroaryl group as described herein. The term "amide" as used herein is generally represented by the formula: $R^1(CO)NR^2R^3$, where either or both $R^2$ and $R^3$ may be hydrogen. An amide is an amine where one of the nitrogen substituents is an acyl group. A "thioamide" as used herein is generally represented by the formula: $R^1(CS)NR^2R^3$, where either or both $R^2$ and $R^3$ may be hydrogen.

The term "alkylamino" refers to a secondary amine substituent with one hydrogen and one alkyl group directly attached to a trivalent nitrogen atom. In addition, the term "alkylamino" also refers to a tertiary amine substituent with two of the same or different alkyl groups directly attached to a trivalent nitrogen atom. The alkyl group is the same as described herein.

The term "alkylamido" refers to substituents of the formula, —C(O)NRR' or —NRC(O)R', in which R and R' are the same or different and each is a hydrogen or alkyl group, as described herein. The term "haloalkylamido" is an alkylamido as described above, in which one or more of the alkyl groups is substituted with a halo moiety, such as, for example, chlorine, bromine or iodine.

The term "amino acid-containing group" refers to substituents that include both a carboxyl group (C(O)OH) and an amino group ($NH_2$). Commonly, such substituents have the generic formula, —$RCH(NH_2)CO_2H$, in which the substituent bonds to a compound through the R group. While any amino acid is to be considered (e.g., glycinyl, alaninyl, leucinyl, etc.) acceptable as a substituent, asparate (—CH($NH_2$)$CO_2H$) and glutamate (—$CH_2CH(NH_2)CO_2H$) are especially preferred. Therefore, when any substituent of (I)-(IX) is asparate or glutamate, the entire nitrogen substituent forms aspartic acid or glutamic acid, respectively.

Also, unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture.

Other objects and advantages will be apparent to those skilled in the art from the following detailed description taken in conjunction with the appended claims and drawings.

BRIEF DESCRIPTION OF THE DRAWINGS

FIGS. 2-16 illustrate exemplary detailed reaction schemes according to embodiments of this invention.

FIG. 2 is a reaction scheme of bifunctional DTPA analogue synthesis.

FIG. 3 is a reaction scheme for bifunctional 1B4M-DTPA.

FIG. 4 is a reaction scheme of 3p-C-NETA analogue synthesis.

FIG. 5 is a reaction scheme demonstrating stereoselective and regioselective ring opening of the aziridinium ion in the synthesis of tetrahydroisoquinoline.

FIG. 6 is a reaction scheme illustrating concise synthesis of nomifensine.

FIG. 7 is a reaction scheme demonstrating stereoselective and regioselective ring opening of the aziridinium ion in the synthesis of tryptamine analogue (R)-5.

FIG. 8 is a reaction scheme demonstrating stereoselective and regioselective ring opening of the aziridinium ion in the synthesis of chiral α-branched amines.

FIG. 9 is a reaction scheme illustrating concise synthesis of (R)-selegiline.

FIG. 10 is a reaction scheme demonstrating stereoselective and regioselective ring opening of the aziridinium ion with Grignard reagents in the synthesis of chiral α-branched amines.

FIG. 11 is a reaction scheme demonstrating regioselective ring opening of the aziridinium ion in the synthesis of γ-aminobutyric acid (GABA) analogues.

FIG. 12 is a reaction scheme illustrating concise synthesis of enantiopure (R)-phenibut.

FIG. 13 is a reaction scheme illustrating synthesis of enantiomerically enriched oxomorpholine 3.

FIGS. 14 and 15 are reaction schemes demonstrating stereoselective and regioselective reactions of aziridinium ions with different nucleophiles, according to additional embodiments of this invention.

FIG. 16 is a reaction scheme demonstrating stereoselective and regioselective ring opening of aziridinium ion in a convenient "one-pot" synthesis of enantiomerically enriched amines with functionally.

DETAILED DESCRIPTION OF THE INVENTION

Figure 1:
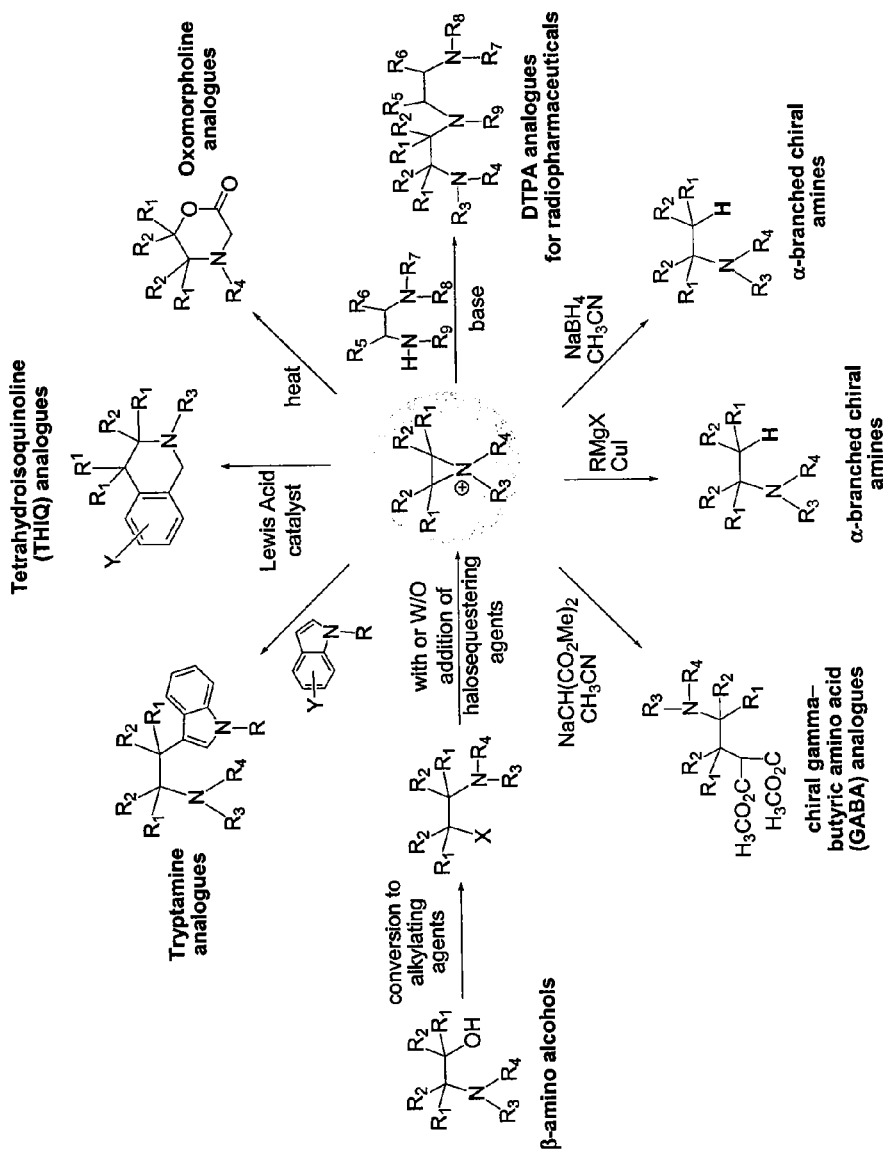
FIG. 1 shows a brief summary of various nucleophilic addition reactions of the aziridinium ion according to embodiments of this invention.

The present invention provides methods of stereoselective or regioselective synthesis of compounds for biomedical applications, and more particularly, for example, therapeutic and/or diagnostic drug compounds. As shown in the general illustration of FIG. 1, the method according to one embodiment of this invention provides an efficient synthesis of numerous compounds based upon a regioselective and/or stereoselective ring opening of aziridinium ions. In one embodiment of the invention, the method includes stereoselectively or regioselectively reacting an aziridinium ion in a nucleophilic ring opening reaction to obtain the desired compound. The resulting compound can be controlled by one or more factors including, without limitation, the substituents of the aziridinium ion, the reagents and reaction conditions, and/or the structure of any nucleophile used in the reaction.

The aziridinium ion can be obtained by intramolecular reaction of a substituted alkylating agent that is converted from a substituted β amino alcohol. In one embodiment of the invention, a substituted β amino alcohol is converted to the substituted aziridinium ion:

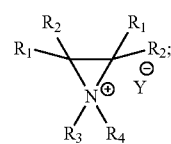

where: Y is a non-nucleophilic counter anion or a leaving group comprising halide, perchlorate, tetrafluoroborate, hexafluoroantimonate, mesylate, triflate, carbonate, nitrate, phthalimide, or succinimide; each of $R_{1-5}$ independently is or includes hydrogen, carboxyalkyl, alkylamido, alkyl, allyl, benzyl, benzyloxyalkyl, cycloalkyl, heterocyclyl, alkoxy, hydroxyalkyl, aryl, CH$_2$Ar, aryloxy, hydroxyaryl, heteroaryl, phenyl, vinyl, alkynyl, alkenyl, substituted carbonyl, halo, haloalkyl, nitrile, oxo, substituted oxo, substituted silyl, thiol, benzhydryl, silyl, substituted carboxyl, hydroxyalkyl, aminoalkyl, alkoxycarbonyl, alkylamido, furannylalkyl, alkylthioalkyl, arylhydroxyalkyl, indanyl, indolylalkyl, naphthylalkyl, imidazolylalkyl, pyridiylalkyl, phthalimidyl, maleimidyl, benzothiophenylalkyl, thiophenylalkyl, thioalkyl, thioaryl, thiobenzyl, hydroxy, hydroxyalkyl, aminoalkyl, tosyl, nosyl, a protected amine, carboxyl, carboxyalkyloxy, amino, carboxylic acid, holoalkylamido, aldehyde, alkylamino, amido, trityl, tert-butyloxycarbonyl, carbobenzyloxy, acetyl, dimethoxybenzyl, p-methoxybenzyl, an amide containing group, a thioamide containing group, an amino acid-containing group, an ester containing group, an amine protecting group; any two vicinal carbons of R$_1$ and R$_2$ together form a fused ring —(CH$_2$)$_n$—; any of R$_{1-5}$ is or attached to chiral carbon; or two germinal carbons, R$_1$ and R$_2$ are bonded together and form a spiro ring or one of:

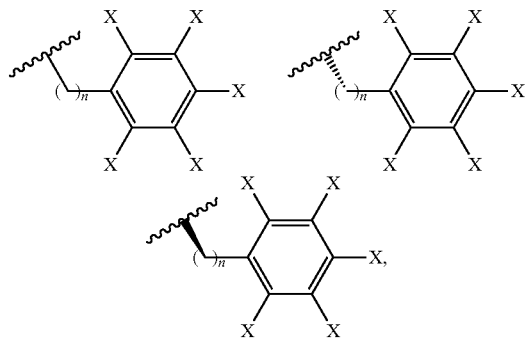

where n=1-10 and X is or includes hydrogen, halo, cyano, alkyl, aryl, hydroxyl, nitro, amino, alkylamino, dialkylamino, substituted amine, substituted carbonyl, isocyanate, cyanate ester, protected amine, protected hydroxyl, protected carboxyl, boronic acid, borinic acid, borinate ester, triflate, silyl, substituted silyl, thiocyano, isothiocyano, alkoxy, aryloxy, carboxyl, carboxylic acid, carboxyalkyl, carboxyalkyloxy, ester, amido, aldehydro, alkylamido, holoalkylamido, an ester containing group, an carbonyl containing group, a boron containing group, a tin containing group, an amide containing group, a thioamide containing group, or an amino acid-containing group. R$_3$ can alternatively be:

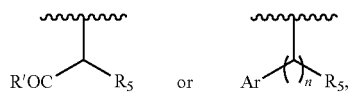

where Ar is an aromatic ring and n=1~3; R' independently is OH, NH$_2$, NR''$_2$, or OR'', wherein R'' independently is alkyl, tert-butyl, allyl, benzyl, CH$_2$Ar, silyl, trityl, an amine protecting group, a carboxyl protecting group, or a hydroxyl protecting group.

In one particularly preferred embodiment, a substituted β amino alcohol is first converted to a substituted alkylating agent, and the substituted alkylating agent is converted to the substituted aziridinium ion. The resulting aziridinium ion is then stereoselectively or regioselectively reacted with a nucleophile to obtain the desired compound. One exemplary substituted alkylating agent is a substituted β-amino halide such as:

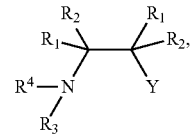

where Y is a halogen, such as, for example, chlorine, bromine, or iodine. In one embodiment of this invention, the substituted alkylating agent is converted to the aziridinium ion in the presence of halosequestering agent, such as, for example, AgClO$_4$, AgOTf, Ag$_2$CO$_3$, AgOTs, AgNO$_3$, AgSbF$_6$, or AgBF$_4$.

Any suitable nucleophile can be used in the method of this invention, depending on need and the desired resulting compound. The aziridinium ion and nucleophile can be reacted in situ by adding the nucleophile to the aziridinium ion solution to obtain the compound. One benefit of the method of this invention is that the reactions can be performed without isolation of any intermediate compound for further reaction.

The method of this invention can be used to prepare analogues of NETA, NE3TA, NE3TA-Bn, N-NE3TA, DEPA, NOTA, DOTA, and DTPA, such as disclosed in U.S. Pat. Nos. 7,163,935 and 7,368,100, and U.S. Patent Application Publication 2010/0322855, each herein incorporated by reference in the entirety. One embodiment of the invention includes stereoselectively or regioselectively reacting the aziridinium ion with a nucleophile selected from:

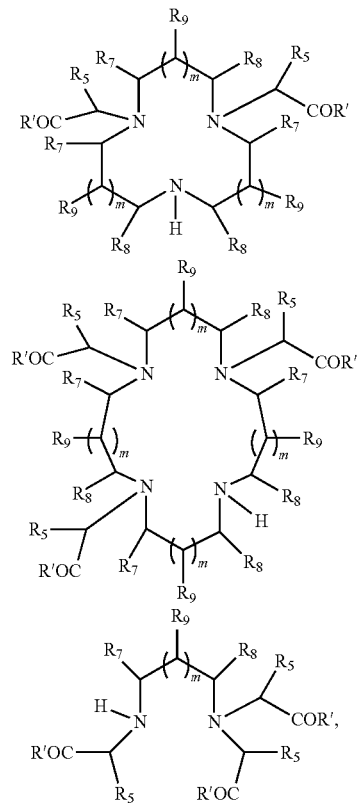

where m is 0 or 1 and R' independently is OH, $NH_2$, $NR_2''$, or OR", wherein R" independently is alkyl, tert-butyl, allyl, benzyl, $CH_2Ar$, silyl, trityl, an amine protecting group, a carboxyl protecting group, or a hydroxyl protecting group, and each of $R_{7-9}$ are as defined above for $R_{1-5}$ of the aziridinium ion, any two vicinal carbons of $R_{7-9}$ together form a fused ring $—(CH_2)_n—$, and/or any of $R_{7-9}$ is or attached to chiral carbon or one of:

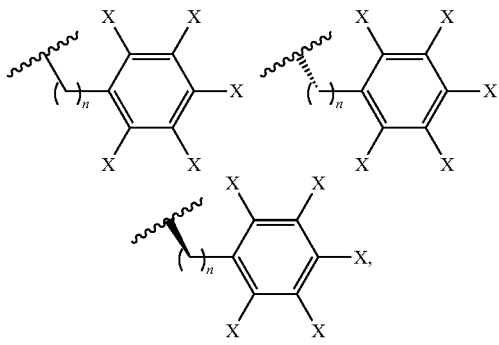

where X is as defined above. The resulting compound can be one of:

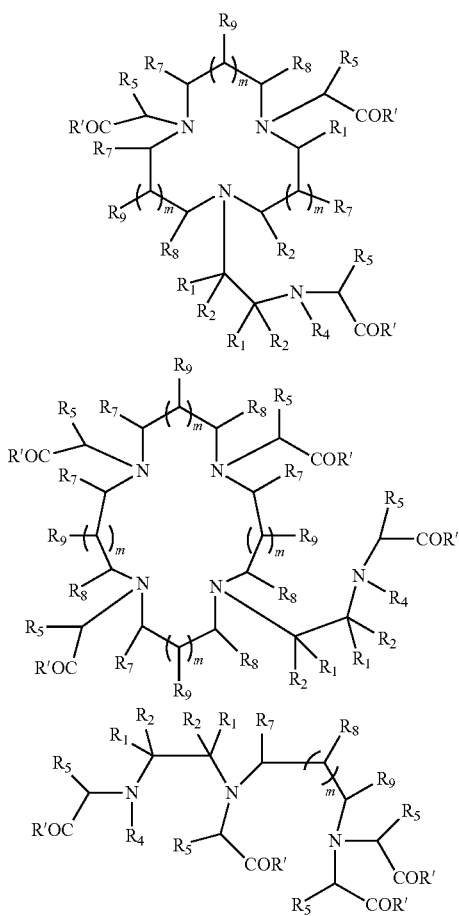

Figure 2:
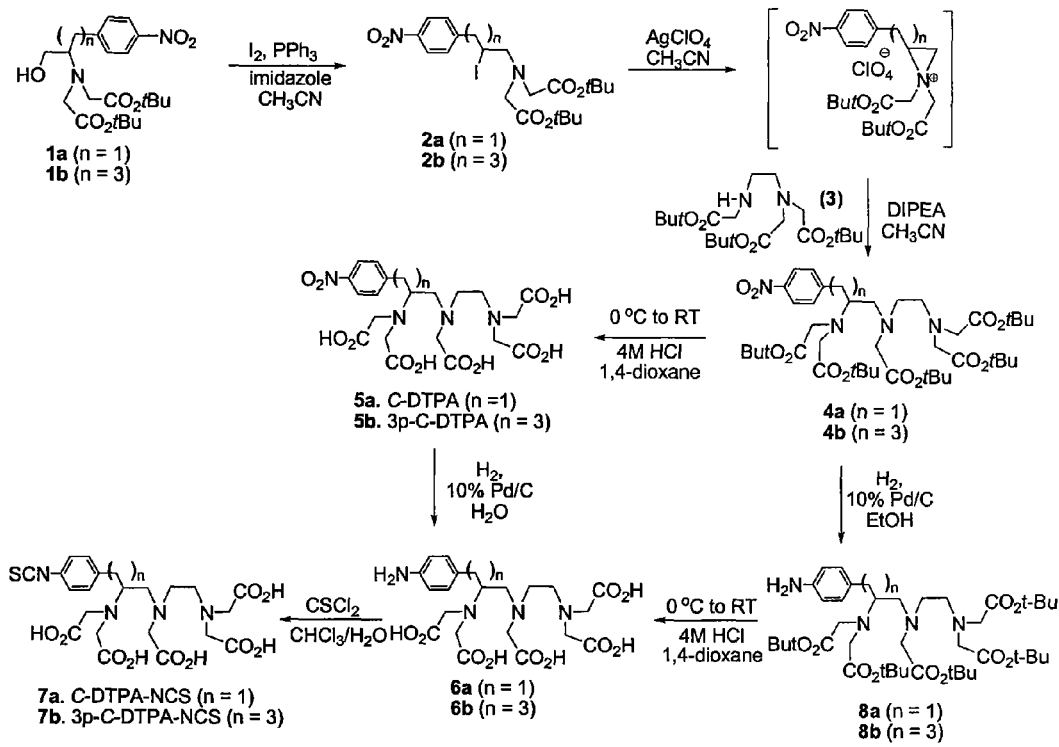
Figure 3:
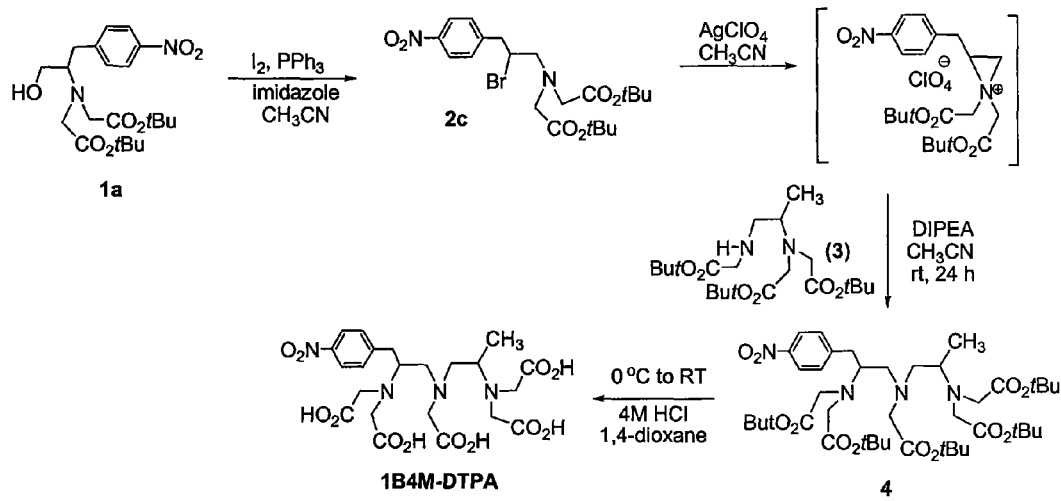
Figure 4:
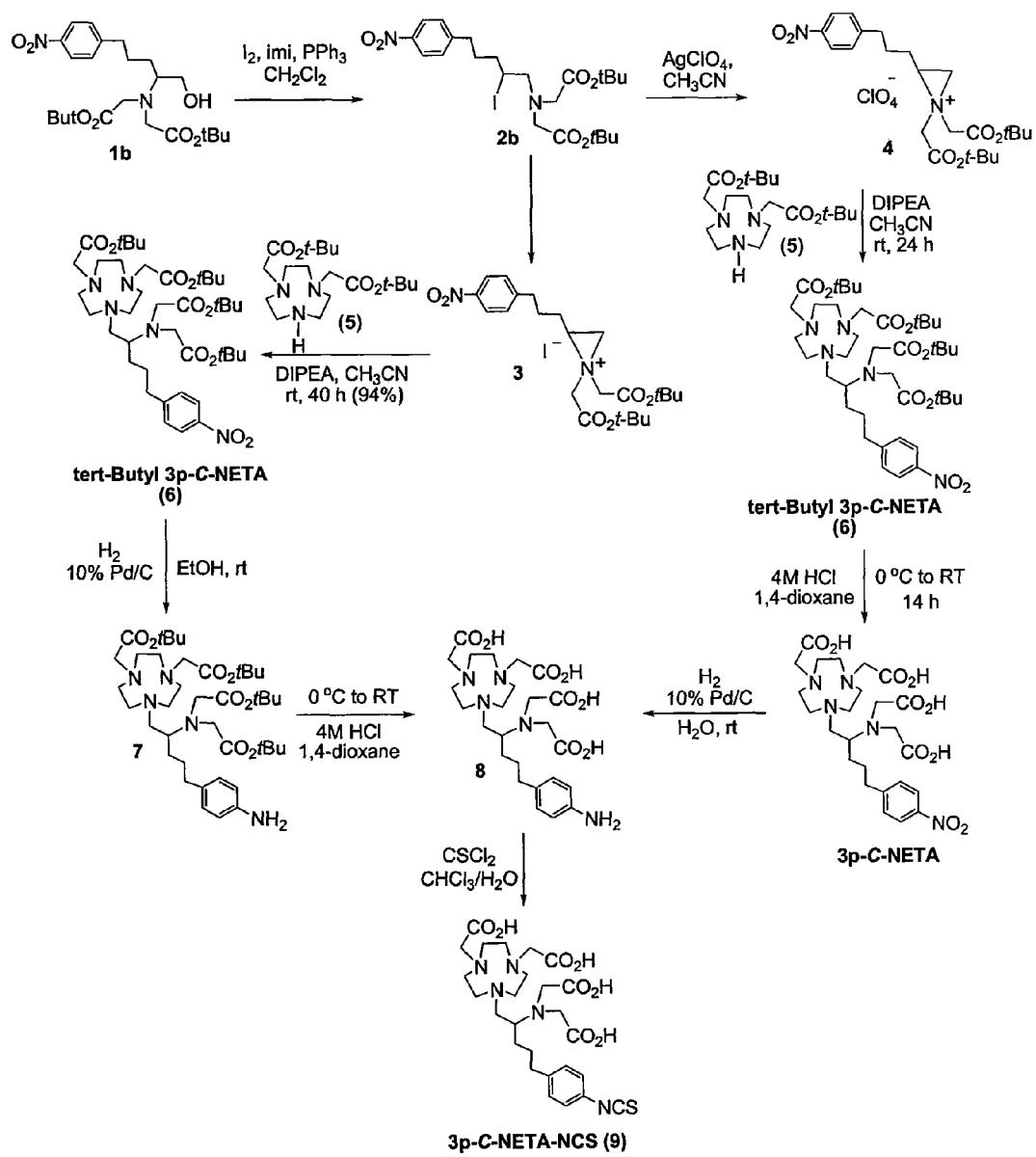

The method can further include a step of removing a protecting group comprising an amino, a carboxyl, or a hydroxyl protecting group from the compound using a deprotection reaction. In some embodiments, a nitro group in the compound can be converted to an amino group, such using hydrogenation with hydrogen on palladium on carbon mixed with water. An amino group can also be converted to an isothiocyanate group. FIGS. 2-4, explained further in the examples below, illustrate exemplary reaction schemes providing DTPA and NETA analogues.

In one embodiment of this invention, the ring opening reaction of the aziridinium ion is performed in the presence of a catalyst. Suitable catalysts include, without limitation, Lewis acids, organocatalysts, or combinations thereof. Exemplary Lewis acids include $AlX_3$, $FeX_3$, $SiX_4$, $ZnX_2$, $TiX_4$, $ZrX_4$, $InX_3$, $CuX_2$, $AuX_3$, $SnX_4$, and $ScX_3$, where X is hydrogen, alkyl, aryl, halo, heterocycle, alkoxy, triflate, hydroxyl, protected amine, alkylated amine. The reaction is typically conducted in situ in an organic solvent.

Figure 6:
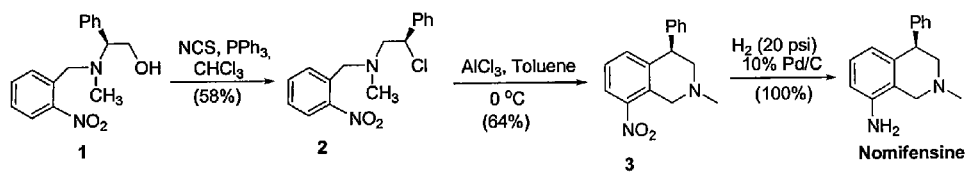

The nucleophile can be provided by or part of the aziridinium ion itself, such as to provide an intramolecular stereoselective or regioselective reaction of the aziridinium ion in the presence of the catalyst. In one embodiment of this invention, the resulting compound of the intramolecular reaction in the presence of a catalyst is one of:

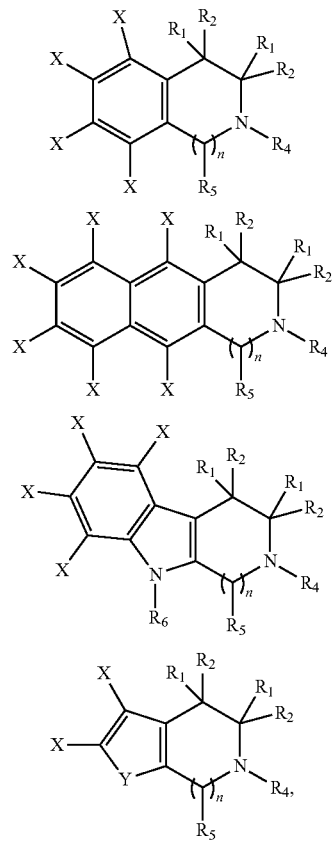

where: n=1, 2, or 3; Y=O, NH, or S; each of each of $R_{1-5}$ and X are as defined above, and $R_6$ is as defined for $R_{1-5}$. FIGS. 5 and 6 illustrate exemplary reactions using a catalyst.

Figure 7:
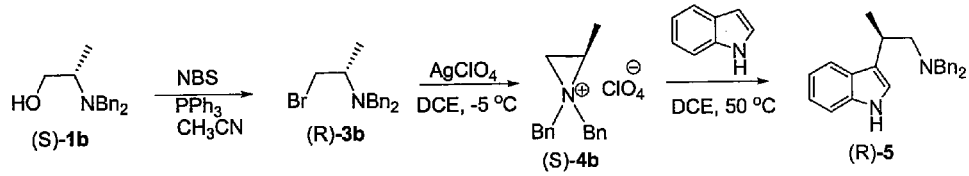

In one embodiment of this invention, the method includes stereoselectively or regioselectively reacting in the presence of a catalyst such as a Lewis acid and/or an organocatalyst, the aziridinium ion with an aromatic compound including:

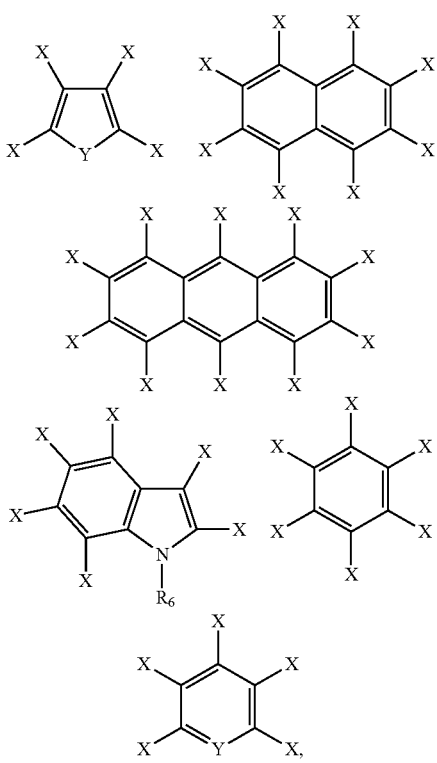

where X is defined as above; Y is NH, O, or S. The aziridinium ion can be formed in situ from reaction of an alkylating agent with a halosequestering agent, and further reacted with the aromatic compound. FIG. 7 illustrates an exemplary reaction by which the aziridinium ion ring is opened using iodole, and resulting in the synthesis of a tryptamine analogue.

Figure 8:
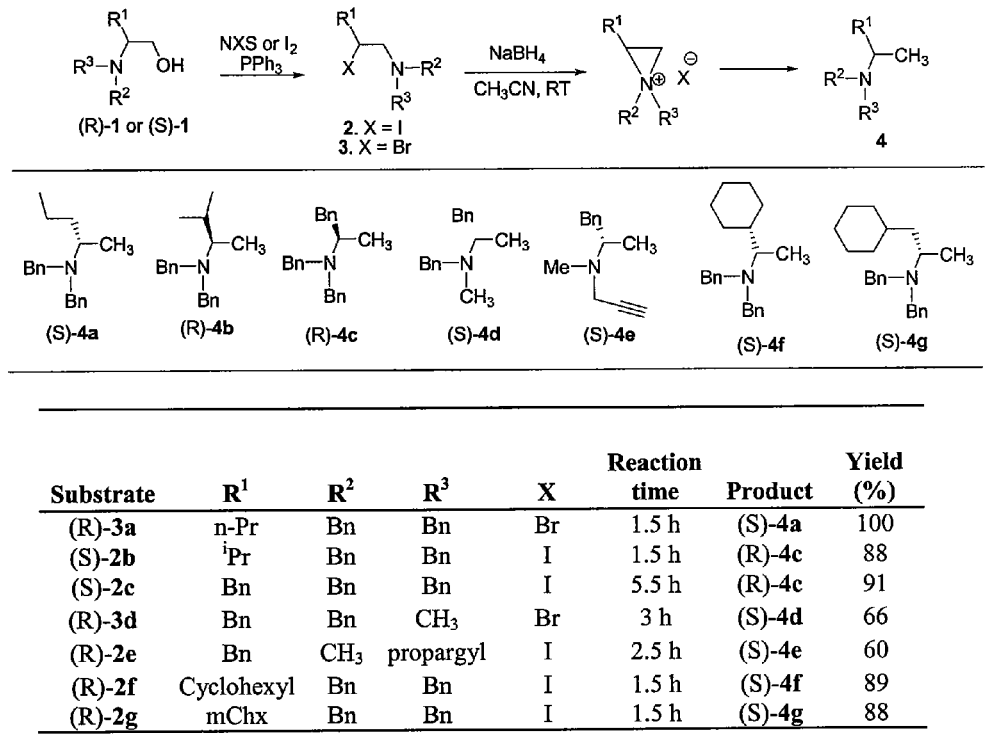
Figure 9:
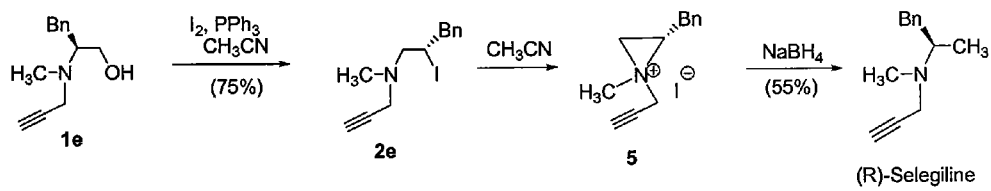
Figure 10:
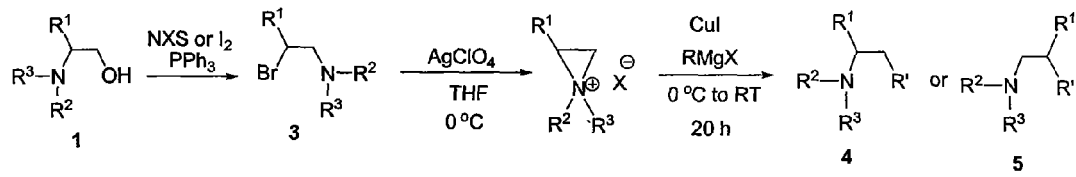

In one embodiment of this invention, the method is used to synthesize a chiral alpha amine. The method can include stereoselectively or regioselectively reacting the aziridinium ion with a reducing agent comprising hydride. This reaction also can be performed in the presence of a catalyst, and preferably an organocatalyst. FIGS. 7 and 8 illustrate exemplary reactions forming a chiral alpha amine, including the enantipure (R)-Selegiline. A chiral alpha amine can also be prepared by stereoselectively or regioselectively reacting the aziridinium ion with an organometallic compound, such as Grignard reagents. The reaction can also be performed in the presence of a catalyst, and preferably an organocatalyst. FIG. 10 illustrates an exemplary reaction using Grignard reagents to produce chiral α-branched amines. As discussed above, the aziridinium ion can be formed in situ from reaction of an alkylating agent with a halosequestering agent in situ and further reacted to form the chiral alpha amine.

Figure 11:
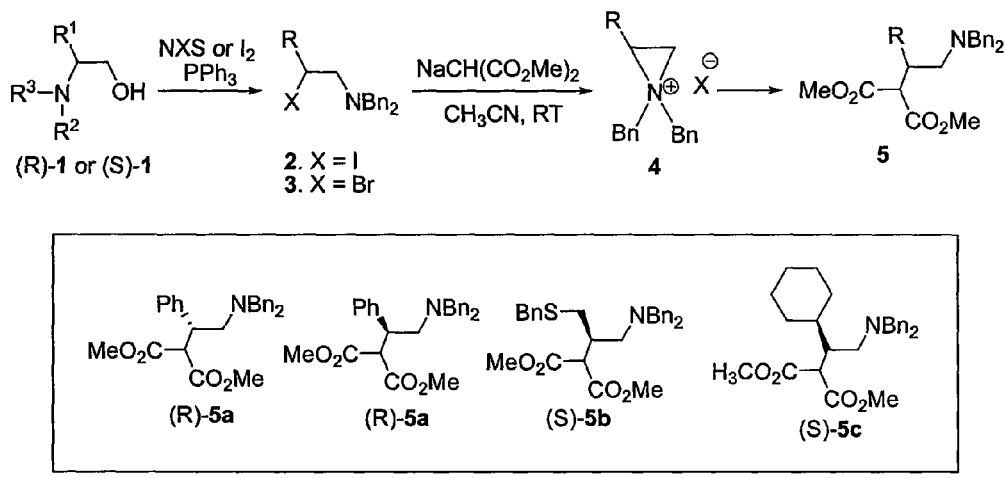
Figure 12:
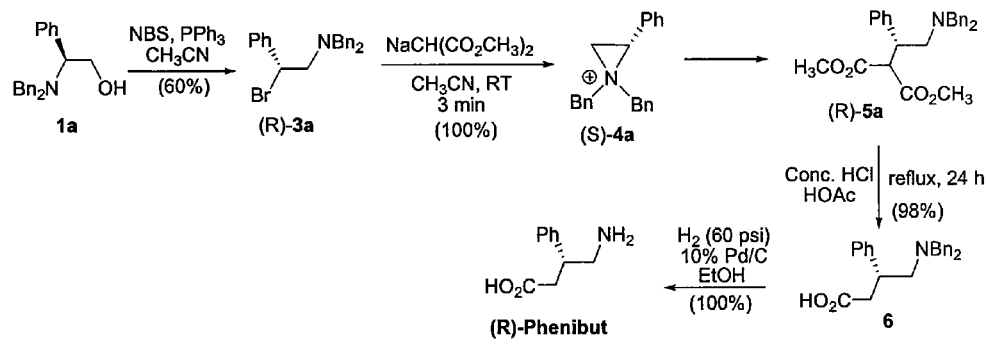

The method of this invention can also be used to synthesize substituted gamma-aminobutyric acid compounds. The aziridinium ion is stereoselectively or regioselectively reacted with a dialkyl malonic ester analogue, such as sodium dimethyl malonate. The reaction is done in the presence of a catalyst, preferably an organocatalyst. FIG. 11 illustrates an exemplary reaction scheme providing optically active γ-aminobutyric acid (GABA) analogues. FIG. 12 illustrates an exemplary synthesis of enantiopure (R)-phenibut.

Figure 13:
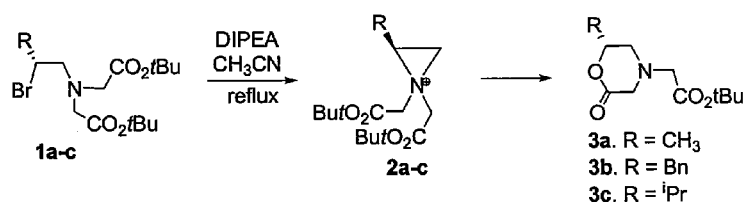
Figure 14:
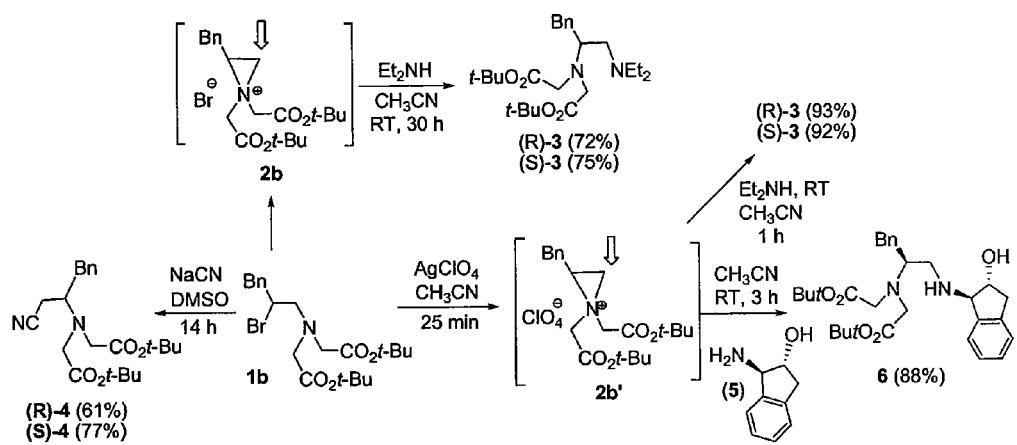
Figure 16:
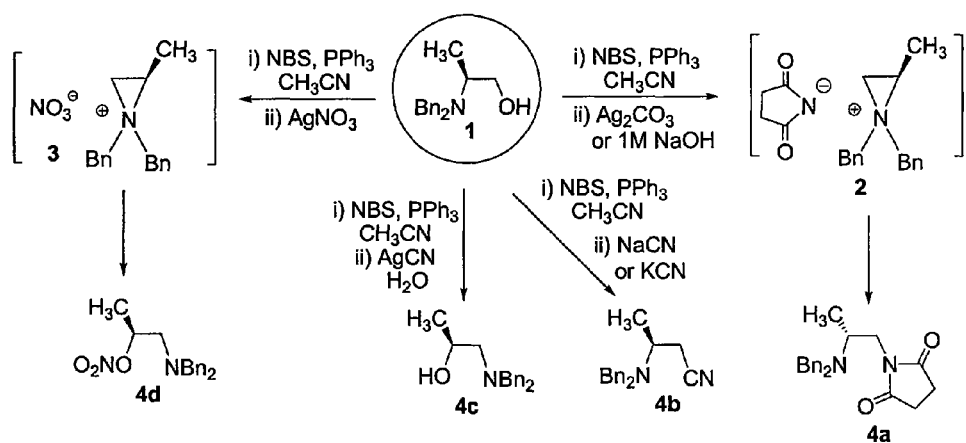

FIGS. 13-16 illustrate additional intramolecular, intermolecular, and/or in situ reactions according to embodiments of this invention. FIG. 13 illustrates an intramolecular stereoselective or regioselective reaction of the aziridinium ion that produce a heterocyclic compound, particularly enantiomerically enriched oxomorpholine 3, in the presence of a catalyst. FIG. 14 is a reaction scheme that includes converting substituted β-amino bromide to the aziridinium ion in the presence or in the absence of the halo-sequestering agent ($AgClO_4$) in situ and reacting the aziridinium ion with a nucleophile to produce the compound. The substituted alkylating agent is treated with a halo-sequestering agent to produce the aziridinium ion containing a non-nucleophilic anion, and the reaction between the aziridinium ion and the nucleophile occurs in situ. The reaction occurs without isolation of any intermediate compound including the aziridinium ion and the substituted alkylating agent to produce the compound. FIG. 15 shows a reaction scheme wherein β-2-phenylglycinol analogues are converted to a β-bromophenethylamine analogue for reaction with various nucleophiles via stereoselective and regiospecific ring opening to produce the optically active compounds. FIG. 16 shows a "one-pot" reaction for synthesis of enantiomerically enriched amines with functionality, wherein the substituted β-amino bromide is produced and converted to the substituted aziridinium ion in the presence or in the absence of a halo-sequestering agent (e.g., AgCN, $Ag_2CO_3$, or $AgNO_3$) that is further reacted with a nucleophile in situ. In the one-pot reactions, no intermediate compounds were isolated, and the desired product was directly synthesized from β-amino alcohol.

In one embodiment of this invention, the aziridinium ion is racemic and reacted with the nucleophile to provide an enantioselective nucleophilic addition product. This type of reaction generally requires a catalyst, such as an organocatalyst or Lewis acid catalyst, or combinations thereof. Racemic aziridinium ions can be used for reactions discussed above with nucleophiles to produce, for example, a chiral product.

The present invention is described in further detail in connection with the following examples which illustrate or simulate various aspects involved in the practice of the invention. It is to be understood that all changes that come within the spirit of the invention are desired to be protected and thus the invention is not to be construed as limited by these examples.

EXAMPLES

Example 1

FIG. 2—Synthesis of C-DTPA Analogues

Experimental tert-butyl 2-{[2-(tert-butoxy)-2-oxoethyl][2-iodo-3-(4-nitrophenyl)propyl]amino}acetate (2a)

To a solution of 1a (500 mg, 1.178 mmol) and $PPh_3$ (370.9 mg, 1.414 mmol) in $CH_2Cl_2$ (5 mL) at 0° C. was added imidazole (96.3 mg, 1.414 mmol) and iodine (358.9 mg, 1.414 mmol) portionwise over 5 min. The reaction mixture was stirred at 0° C. for 4 h and RT for 1 h after which the reaction mixture was concentrated to dryness. The residue was purified by silica gel (60-230 mesh) column chromatography eluted with 10% ethyl acetate in hexanes to afford 2a (603 mg, 95%) as a brownish oil. $^1$H NMR ($CDCl_3$, 300 MHz) δ 1.45 (s, 18H), 2.90-3.07 (m, 2H), 3.31-3.57 (m, 5H), 3.76-3.90 (m, 1H), 4.10-4.27 (m, 1H), 7.40 (d, J=8.6 Hz, 2H), 8.13 (d, J=8.6 Hz, 2H); $^{13}$C NMR (CDCl$_3$, 300 MHz) δ 28.2 (q), 34.8 (d), 42.9 (t), 57.2 (t), 64.5 (t), 81.4 (s), 123.5 (d), 130.4 (d), 146.7 (s), 147.9 (s), 170.5 (s).

tert-butyl 2-{[2-(tert-butoxy)-2-oxoethyl][2-iodo-5-(4-nitrophenyl)pentyl]amino}acetate (2b)

To a solution of 1b (100 mg, 0.221 mmol) and PPh$_3$ (69.5 mg, 0.265 mmol) in CH$_2$Cl$_2$ (2 mL) at 0° C. was added imidazole (18 mg, 0.265 mmol) and iodine (67.3 mg, 0.265 mmol) portionwise over 5 min. The reaction mixture was stirred at 0° C. for 4 h and RT for 1 h after which the reaction mixture was concentrated to dryness. The residue was purified by silica gel (60-230 mesh) column chromatography eluted with 10% ethyl acetate in hexanes to afford 2b (120 mg, 97%) as a brownish oil. $^1$H NMR (CDCl$_3$, 300 MHz) δ 1.45 (s, 18H), 1.71-1.82 (m, 2H), 1.83-2.05 (m, 2H), 2.66-2.87 (m, 2H), 2.90-3.01 (m, 1H), 3.23-3.36 (m, 1H), 3.36-3.50 (m, 4H), 4.10-4.18 (m, 1H), 7.35 (d, J=8.6 Hz, 2H), 8.14 (d, J=8.6 Hz, 2H); $^{13}$C NMR (CDCl$_3$, 300 MHz) δ 28.2 (q), 30.8 (t), 34.9 (t), 36.0 (d), 36.3 (t), 56.9 (t), 64.1 (t), 81.2 (s), 123.6 (d), 129.2 (d), 146.4 (s), 149.9 (s), 170.4 (s). HRMS (Positive ion FAB) Calcd for C$_{23}$H$_{36}$IN$_2$O$_6$: [M−I+OH]$^+$ m/z 453.2601. Found: [M−I+OH]$^+$ m/z 453.2603.

tert-butyl 2-[(2-{bis[2-(tert-butoxy)-2-oxoethyl]amino}-3-(4-nitrophenyl)propyl)(2-{bis[2-(tert-butoxy)-2-oxoethyl]amino}ethyl)amino]acetate (4a)

To a solution of 2a (520 mg, 0.956 mmol) in CH$_3$CN (2 mL) at −5° C. was added AgClO$_4$ (198.2 mg, 0.956 mmol) and stirred for 15 min at the same temperature. Then, compound 3 (384.8 mg, 0.956 mmol) and DIPEA (370.8 mg, 2.87 mmol) in CH$_3$CN (2 mL) was sequentially added to the reaction mixture at −5° C. The resulting mixture was warmed to room temperature and stirred for 14 h while monitoring the reaction progress using TLC. The resulting mixture was filtered and evaporated to dryness. Then 0.1M HCl solution (30 mL) was added to the residue and extracted with CHCl$_3$ (30 mL×3). The combined organic layers were concentrated to dryness. The residue was washed with 0.1M NaOH solution (30 mL) and extracted with CHCl$_3$ (30 mL×3). The basic wash step was repeated 5 times until no more black silver salt appeared. The combined organic layers were dried over MgSO$_4$, filtered, and concentrated in vacuo to the dryness to provide pure product 4a (770 mg, 99%) as a yellowish oil. $^1$H NMR (CDCl$_3$, 300 MHz) δ 1.40 (s, 27H), 1.42 (s, 18H), 2.43 (dd, J=13 Hz, 8.3 Hz, 1H), 2.52-3.18 (m, 8H), 3.20-3.50 (m, 10H), 7.47 (d, J=8.7 Hz, 2H), 8.08 (d, J=8.7 Hz, 2H); $^{13}$C NMR (CDCl$_3$, 300 MHz) δ 28.1 (q), 28.2 (q), 29.7 (t), 37.3 (t), 52.1 (t), 53.1 (t), 53.3 (t), 55.9 (t), 56.2 (t), 62.8 (d), 80.8 (s), 80.9 (s), 123.3 (d), 130.3 (d), 146.2 (s), 149.1 (s), 170.5 (s), 170.6 (s), 171.1 (s).

tert-butyl 2-[(2-{bis[2-(tert-butoxy)-2-oxoethyl]amino}-5-(4-nitrophenyl)pentyl)(2-{bis[2-(tert-butoxy)-2-oxoethyl]amino}ethyl)amino]acetate (4b)

To a solution of 2b (200 mg, 0.388 mmol) in CH$_3$CN (0.5 mL) at −5° C. was added AgClO$_4$ (80.4 mg, 0.388 mmol) and stirred for 15 min at the same temperature. Then, compound 3 (156.2 mg, 0.388 mmol) and DIPEA (150.4 mg, 1.164 mmol) in CH$_3$CN (1 mL) was sequentially added to the reaction mixture at −5° C. The resulting mixture was warmed to room temperature and stirred for 24 h while monitoring the reaction progress using TLC. The reaction mixture was filtered and evaporated to dryness. The residue was purified via column chromatography on silica gel (60-230 mesh) eluting with 20% ethyl acetate in hexanes to provide the pure product 4b (251 mg, 77%) as a yellowish oil. $^1$H NMR (CDCl$_3$, 300 MHz) δ 1.35-1.43 (m, 45H), 1.44-1.95 (m, 4H), 2.20-2.38 (m, 1H), 2.55-2.85 (m, 8H), 3.16-3.47 (m, 10H), 7.33 (d, J=8.7 Hz, 2H), 8.08 (d, J=8.7 Hz, 2H); $^{13}$C NMR (CDCl$_3$, 300 MHz) δ 27.9 (t), 28.1 (q), 28.2 (q), 30.6 (t), 35.8 (t), 52.2 (t), 53.1 (t), 56.0 (t), 56.1 (t), 56.4 (t), 60.1 (d), 80.5 (s), 80.9 (s), 123.5 (d), 129.3 (d), 146.1 (s), 151.0 (s), 170.5 (s), 170.6 (s), 171.4 (s).

2-({2-[bis(carboxymethyl)amino]-3-(4-nitrophenyl)propyl}({2-[bis(carboxymethyl)amino]ethyl})amino)acetic acid (5a)

To a flask containing compound 4a (50 mg, 0.0618 mmol) at 0-5° C. was added dropwise 4M HCl (g) in 1,4-dioxane (3 mL) over 10 min. The resulting mixture was gradually warmed to room temperature and continuously stirred for 40 h. Ether (20 mL) was added to the reaction mixture which was then stirred for 10 min. The resulting precipitate was filtered and washed with ether. The solid product was quickly dissolved in deionized water. The aqueous solution was concentrated in vacuo to provide 5a (40 mg, 100%) as an off-white solid. $^1$H NMR (D$_2$O, 300 MHz) δ 2.63-2.82 (m, 1H), 2.96-3.40 (m, 7H), 3.40-4.05 (m, 11H), 7.39 (d, J=8.1 Hz, 2H), 8.09 (d, J=7.8 Hz, 2H); $^{13}$C NMR (D$_2$O, 300 MHz) δ 32.7 (t), 50.2 (t), 50.7 (t), 52.5 (t), 54.0 (t), 54.9 (t), 55.3 (t), 61.1 (d), 124.1 (d), 130.3 (d), 144.5 (s), 146.8 (s), 170.4 (s), 170.9 (s), 173.5 (s).

2-({2-[bis(carboxymethyl)amino]-5-(4-nitrophenyl)pentyl}({2-[bis(carboxymethyl)amino]ethyl})amino)acetic acid (5b)

To a flask containing compound 4b (30 mg, 0.0358 mmol) at 0-5° C. was added dropwise 4M HCl (g) in 1,4-dioxane (2 mL) over 10 min. The resulting mixture was gradually warmed to room temperature and continuously stirred for 40 h. Ether (20 mL) was added to the reaction mixture which was then stirred for 10 min. The resulting precipitate was filtered and washed with ether. The solid product was quickly dissolved deionized water. The aqueous solution was concentrated in vacuo to provide 5b (24 mg, 100%) as an off-white solid. $^1$H NMR (D$_2$O, 300 MHz) δ1.03-1.89 (m, 4H), 2.21-4.32 (m, 20H), 7.27 (s, 2H), 7.97 (s, 2H); $^{13}$C NMR (D$_2$O, 300 MHz) δ25.0 (t), 26.3 (t), 34.6 (t), 46.9 (t), 48.7 (t), 52.3 (t), 52.7 (t), 53.6 (t), 54.6 (t), 55.3 (t), 62.4 (d), 123.7 (d), 129.4 (d), 145.9 (s), 150.0 (s), 168.5 (s), 170.5 (s), 172.7 (s).

2-{[3-(4-aminophenyl)-2-[bis(carboxymethyl)amino]propyl]({2-[bis(carboxymethyl)amino]ethyl})amino}acetic acid (6a)

To a solution of 5a (32 mg, 0.0502 mmol) in H$_2$O (9 mL) at room temperature was added 10% Pd/C (13 mg) under Ar (g). The reaction mixture was placed under hydrogenation apparatus for 24 h. The resulting mixture was filtered via celite bed and washed thoroughly with H$_2$O. The filtrate was concentrated to provide 6a (30 mg, 93%) as a yellowish solid. $^1$H NMR (D$_2$O, 300 MHz) δ 2.43-4.25 (m, 22H), 7.21 (s, 4H).

2-{[5-(4-aminophenyl)-2-[bis(carboxymethyl)amino]pentyl]({2-[bis(carboxymethyl)amino]ethyl})amino}acetic acid (6b)

To a solution of 5b (36 mg, 0.0541 mmol) in ethanol (9 mL) at room temperature was added 10% Pd/C (10 mg)

under Ar (g). The reaction mixture was placed under hydrogenation apparatus for 24 h. The resulting mixture was filtered via celite bed and washed thoroughly with methanol. The filtrate was concentrated to provide 6b (33 mg, 91%) as a yellowish solid. $^1$H NMR (D$_2$O, 300 MHz) δ1.03-2.15 (m, 5H), 2.20-4.40 (m, 18H), 7.38 (s, 4H).

2-({2-[bis(carboxymethyl)amino]-3-(4-isothiocyanatophenyl)propyl}({2-[bis(carboxy methyl)amino] ethyl})amino)acetic acid (7a)

To a solution of 6a (10 mg, 0.0155 mmol) in water (100 μL) was added dropwise 1M thiophosgene in CHCl$_3$ (18.6 μL, 0.0186 mmol). The resulting mixture was stirred at room temperature for 3 h. The aqueous layer was concentrated in vacuo to provide pure 7a (10 mg, 99%) as a light yellowish solid. $^1$H NMR (MeOD, 300 MHz) δ 2.50-4.55 (m, 24H), 7.10-70 (m, 4H).

2-({2-[bis(carboxymethyl)amino]-5-(4-isothiocyanatophenyl)pentyl}({2-[bis(carboxy methyl)amino] ethyl})amino)acetic acid (7b)

To a solution of 6b (10.2 mg, 0.0152 mmol) in water (100 μL) was added dropwise 1M thiophosgene in CHCl$_3$ (18.2 μL, 0.0182 mmol). The resulting mixture was stirred at room temperature for 3 h. The aqueous layer was concentrated in vacuo to provide pure 7b (10 mg, 97%) as a light yellowish solid. $^1$H NMR (MeOD, 300 MHz) δ 2.40-4.51 (m, 28H), 7.05-7.70 (m, 4H).

Example 2

FIG. 3—Synthesis of 1B4M-DTPA

Experimental

To a solution of 2c (175 mg, 0.359 mmol) in CH$_3$CN (1 mL) at −5° C. was added AgClO$_4$ (74.4 mg, 0.359 mmol) and stirred for 15 min at −5° C. Compound 3 (150 mg, 0.359 mmol) and DIPEA (139.2 mg, 1.078 mmol) in CH$_3$CN (2 mL) was sequentially added to the reaction mixture at −5° C. The resulting mixture was warmed to room temperature and stirred for 24 h after which the reaction mixture was filtered and evaporated to dryness. The residue was purified via column chromatography on silica gel (60-230 mesh) eluting with 20% ethyl acetate in hexanes slowly to provide 4 (in 90% purity) as a yellowish oil.

Example 3

FIG. 4—Synthesis of 3p-C-NETA Analogue

Experimental tert-butyl 2-{[2-(tert-butoxy)-2-oxoethyl][2-iodo-5-(4-nitrophenyl)pentyl]amino}acetate (2b)

To a solution of 1b (100 mg, 0.221 mmol) and PPh$_3$ (69.5 mg, 0.265 mmol) in CH$_2$Cl$_2$ (2 mL) at 0° C. was added imidazole (18 mg, 0.265 mmol) and iodine (67.3 mg, 0.265 mmol) portionwise over 5 min. The reaction mixture was stirred for 4 h at 0° C. and RT for 1 h after which the reaction mixture was concentrated to dryness. The residue was purified by silica gel (60-230 mesh) column chromatography eluted with 10% ethyl acetate in hexanes to afford 2b (120 mg, 97%) as a brownish oil. $^1$H NMR (CDCl$_3$, 300 MHz) δ 1.45 (s, 18H), 1.71-1.82 (m, 2H), 1.83-2.05 (m, 2H), 2.66- 2.87 (m, 2H), 2.90-3.01 (m, 1H), 3.23-3.36 (m, 1H), 3.36-3.50 (m, 4H), 4.10-4.18 (m, 1H), 7.35 (d, J=8.6 Hz, 2H), 8.14 (d, J=8.6 Hz, 2H); $^{13}$C NMR (CDCl$_3$, 300 MHz) δ 28.2 (q), 30.8 (t), 34.9 (t), 36.0 (d), 36.3 (t), 56.9 (t), 64.1 (t), 81.2 (s), 123.6 (d), 129.2 (d), 146.4 (s), 149.9 (s), 170.4 (s). HRMS (Positive ion FAB) Calcd for C$_{23}$H$_{36}$IN$_2$O$_6$: [M−I+OH]$^+$ m/z 453.2601. Found: [M−I+OH]$^+$ m/z 453.2603.

tert-butyl-2-[(1-{4,7-bis[2-(tert-butoxy)-2-oxoethyl]-1,4,7-triazonan-1-yl}-5-[4-(hydroxyl-nitro)phenyl] pentan-2-yl)[2-(tert-butoxy)-2-oxoethyl]amino]acetate (6)

To a solution of 2b (50 mg, 0.089 mmol) in CH$_3$CN (1 mL) at 0° C. was added compound 5 (35.0 mg, 0.098 mmol) and DIPEA (34.5 mg, 0.267 mmol). The resulting mixture was stirred for 40 h at room temperature, while monitoring the reaction progress using TLC. The reaction mixture was concentrated to dryness. The residue was purified via column chromatography on silica gel (220-440 mesh) eluting with 3% CH$_3$OH in CH$_2$Cl$_2$ to provide product 6 (65 mg, 94%). $^1$H and $^{13}$C NMR data of 7 were identical to those as previously reported.

tert-butyl-2-[(1-{4,7-bis[2-(tert-butoxy)-2-oxoethyl]-1,4,7-triazonan-1-yl}-5-[4-(hydroxyl-nitro)phenyl] pentan-2-yl)[2-(tert-butoxy)-2-oxoethyl]amino]acetate (6)

Reaction of 2b with 5 in the Presence of AgClO$_4$.

To a solution of 2b (50 mg, 0.089 mmol) in CH$_3$CN (0.5 mL) at −5° C. was added AgClO$_4$ (18.4 mg, 0.089 mmol) and stirred for 10 min at the same temperature. Then, compound 5 (31.8 mg, 0.089 mmol) and DIPEA (34.5 mg, 0.267 mmol) in CH$_3$CN (0.5 mL) was sequentially added to the reaction mixture at −5° C. The resulting mixture was warmed to room temperature and stirred for 24 h while monitoring the reaction progress using TLC. The residue was purified via column chromatography on silica gel (60-230 mesh) eluting with 3% CH$_3$OH in CH$_2$Cl$_2$ to provide the crude product 6 containing a tiny amount of the starting material 5 as an impurity. The crude product was treated with 0.1M HCl solution (10 mL) and extracted with CHCl$_3$ (10 mL×3). The combined organic layers were concentrated to dryness. The residue was treated with 0.1M NaOH solution (10 mL) and extracted with CHCl$_3$ (10 mL×3). The combined organic layers were dried over MgSO$_4$, filtered, and concentrated in vacuo to the dryness to provide product 6 (62 mg, 88%) as a yellowish oil. $^1$H and $^{13}$C NMR data of 6 were identical to those as previously reported.

{4-[5-(4-Aminophenyl)-2-(bis-tert-butoxycarbonyl-methylamino) pentyl]-7-tert-butoxycarbo-nylmethyl-[1,4,7]-triazonan-1-yl}acetic acid tert-butyl ester (7)

To a solution of 6 (14.6 mg, 0.018 mmol) in ethanol (5 mL) at room temperature was added 10% Pd/C (3 mg) under Ar (g). The reaction mixture was placed under hydrogenation apparatus for 14 h. The resulting mixture was filtered via celite bed and washed thoroughly with ethanol. The filtrate was concentrated to provide 7 (13.1 mg, 93%) as a yellowish solid. $^1$H NMR (CDCl$_3$, 300 MHz) δ1.35-1.70 (m, 40H), 1.92-2.05 (m, 1H), 2.18-2.32 (m, 1H), 2.38-2.90 (m, 15H), 3.08 (d, J=16.6 Hz, 1H), 3.26 (d, J=16.5 Hz, 1H), 3.34 (s, 2H), 3.44 (s, 4H), 6.60 (d, J=8.3 Hz, 2H), 6.94 (d, J=8.2 Hz, 2H); $^{13}$C NMR (CDCl$_3$, 300 MHz) δ 27.8 (t), 28.0 (q), 28.1 (t), 28.4 (t), 29.6 (t), 35.8 (t), 51.3 (t), 51.7 (t), 53.5 (t), 54.7 (t), 55.9 (t), 58.1 (t), 58.5 (t), 59.4 (d), 81.2 (s), 81.3 (s), 82.2 (s), 115.2 (d), 119.1 (d), 131.2 (s), 145.5 (s), 170.7 (s), 170.9 (s), 171.4 (s). HRMS (Positive ion FAB) Calcd for $C_{41}H_{72}N_5O_8$: $[M+H]^+$ m/z 762.5381. Found: $[M+H]^+$ m/z 762.5364.

{4-[5-(4-Amino-phenyl)-2-(bis-carboxymethyl-amino)pentyl]-7-carboxymethyl-[1,4,7]triazo-nan-1-yl}acetic acid (8)

To a flask containing compound 7 (8.5 mg, 0.011 mmol) at 0-5° C. was added dropwise 4M HCl (g) in 1,4-dioxane (3 mL) over 20 min. The resulting mixture was gradually warmed to room temperature and continuously stirred for 18 h. Ether (20 mL) was added to the reaction mixture which was then stirred for 10 min. The resulting mixture was placed in the freezer for 1 h. The resulting precipitate was filtered and washed with ether. The solid product was quickly dissolved in deionized water. The aqueous solution was concentrated in vacuo to provide 8 (7.1 mg, 88%) as an off-white solid. $^1$H NMR ($D_2O$, 300 MHz) δ 1.50-1.73 (m, 4H), 2.53-2.65 (m, 2H), 3.00-3.35 (m, 10H), 3.49-3.85 (m, 13H), 7.17-7.30 (m, 4H); $^{13}$C NMR ($D_2O$, 300 MHz) δ 25.7 (t), 26.6 (t), 33.5 (t), 48.2 (t), 49.6 (t), 50.4 (t), 51.8 (t), 52.5 (t), 53.7 (t), 54.0 (t), 56.0 (t), 60.3 (d), 123.0 (d), 127.5 (s), 130.0 (d), 142.2 (s), 168.0 (s), 170.0 (s), 173.6 (s). HRMS (Positive ion FAB) Calcd for $C_{25}H_{40}N_5O_8$: $[M+H]^+$ m/z 538.2877. Found: $[M+H]^+$ m/z 538.2880.

Synthesis of Compound 8 Via Hydrogenation of 3p-C-NETA

To a solution of 3p-C-NETA (10.3 mg, 0.018 mmol) in $H_2O$ (7 mL) at room temperature was added 10% Pd/C (3 mg) under Ar (g). The reaction mixture was placed under hydrogenation apparatus for 5 h. The resulting mixture was filtered via celite bed and washed thoroughly with methanol. The filtrate was concentrated to provide 8 (10.1 mg, 96%) as a yellowish solid. $^1$H and $^{13}$C NMR data of 8 were identical to those described above.

{4-[2-(Bis-carboxymethylamino)-5-(4-isothiocya-natophenyl) pentyl]-7-carboxymethyl-[1,4,7]triazo-nan-1-yl}acetic acid (3p-C-NETA-NCS, 9)

To a solution of 8 (6.3 mg, 0.009 mmol) in water (0.15 mL) was added dropwise 1M thiophosgene in $CHCl_3$ (11 μL, 0.011 mmol). The resulting mixture was stirred at room temperature for 3 h. The aqueous layer was concentrated in vacuo to provide pure 9 (6.0 mg, 95%) as a light yellowish solid. $^1$H NMR ($D_2O$, 300 MHz) δ 1.50-1.75 (m, 4H), 2.50-2.61 (m, 2H), 2.95-4.02 (m, 23H), 7.13 (s, 4H). HRMS (Positive ion FAB) Calcd for $C_{26}H_{38}N_5O_8S$: $[M+H]^+$ m/z 580.2441. Found: $[M+H]^+$ m/z 580.2439.

Example 4

FIG. 5—Synthesis of Tetrahydroisoquinoline (THIQ) Analogues

Experimental

General Procedure for Conversion of β-Amino Alcohol (1) to Secondary β-Amino Halide.

To a solution of N,N-dialkylated alcohol 1 (1 eq) and triphenyl phosphine (1.2 eq) in $CHCl_3$ was added NCS, NBS, or NIS (1.2 eq) portionwise at 0° C. over 20 min. The resulting mixture was stirred for 4 h while being maintained at 0° C. The ice bath was removed, and the reaction mixture was warmed to room temperature and stirred for 1 h and evaporated to dryness. The residue was purified via column chromatography on silica gel (60-230 mesh) eluting with 5-10% EtOAc in hexanes.

Dibenzyl[(2R)-2-chloro-2-phenylethyl]amine((R)-2a)

$^1$H NMR ($CDCl_3$, 300 MHz) δ3.12 (d, J=7.3 Hz, 2H), 3.65 (dd, J=40.1, 13.6 Hz, 4H), 4.85 (t, J=7.4 Hz, 1H), 7.23-7.37 (m, 15H); $^{13}$C NMR ($CDCl_3$, 300 MHz) δ 59.0 (t), 61.1 (d), 61.9 (t), 127.1 (d), 127.6 (d), 128.3 (d), 128.6 (d), 128.9 (d), 129.2 (d), 139.0 (s), 140.4 (s). $[\alpha]^{26}_D=-47.3°$ (c=1.0, $CHCl_3$).

Dibenzyl[(2R)-2-bromo-2-phenylethyl]amine((R)-3a)

$^1$H NMR ($CDCl_3$, 300 MHz) δ3.22 (d, J=7.6 Hz, 2H), 3.61 (dd, J=41.4, 13.5 Hz, 4H), 4.91 (t, J=7.6 Hz, 1H), 7.19-7.31 (m, 15H); $^{13}$C NMR ($CDCl_3$, 300 MHz) δ 52.7 (d), 58.9 (t), 61.6 (t), 127.1 (d), 128.1 (d), 128.3 (d), 128.3 (d), 128.5 (d), 129.0 (d), 139.0 (s), 140.1 (s). $[\alpha]^{26}_D=-60.0°$ (c=1.0, $CHCl_3$).

Dibenzyl[(2S)-2-bromopropyl]amine((S)-3b)

$^1$H NMR ($CDCl_3$, 300 MHz) δ1.65 (d, J=6.6 Hz, 3H), 2.69-2.76 (m, 1H), 2.88-2.95 (m, 1H), 3.65 (dd, J=35.7, 13.5 Hz, 4H), 4.07-4.14 (m, 1H), 7.26-7.42 (m, 10H); $^{13}$C NMR ($CDCl_3$, 300 MHz) δ 24.0 (q), 47.9 (d), 59.1 (t), 62.7 (t), 127.2 (d), 128.3 (d), 129.0 (d), 139.1 (s). $[\alpha]^{26}_D=18.9°$ (c=1.0, $CHCl_3$).

Dibenzyl[(2R)-2-bromo-3-phenylpropyl]amine((R)-3c)

$^1$H NMR ($CDCl_3$, 300 MHz) δ 2.71 (dd, J=14.2, 9.8, 1H), 2.90-2.96 (m, 2H), 3.46 (dd, J=14.5, 3.1 Hz, 1H), 3.66 (dd, J=37.2, 13.3 Hz, 4H), 4.07-4.14 (m, 1H), 7.06-7.40 (m, 15H); $^{13}$C NMR ($CDCl_3$, 300 MHz) δ 42.7 (t), 54.8 (d), 59.4 (t), 61.5 (t), 126.6 (d), 127.2 (d), 128.3 (d), 129.1 (d), 129.2 (d), 138.9 (s), 139.0 (s). $[\alpha]^{26}_D=-12.6°$ (c=1.0, $CHCl_3$).

Bibenzyl[(2S)-2-bromopentyl]amine((R)-3d)

$^1$H NMR ($CDCl_3$, 300 MHz) δ0.88 (t, J=7.4 Hz, 3H), 1.26-1.45 (m, 3H), 1.46-1.64 (m, 1H), 1.89-1.97 (m, 1H), 2.78-2.94 (m, 2H), 3.56-3.71 (dd, J=33.0, 13.5 Hz, 4H), 4.00-4.05 (m, 1H), 7.25-7.41 (m, 10H); $^{13}$C NMR ($CDCl_3$, 300 MHz) δ 13.5 (q), 20.3 (t), 38.2 (t), 54.8 (d), 59.2 (t), 61.4 (t), 127.2 (d), 128.3 (d), 129.0 (d), 139.1 (s). $[\alpha]^{26}_D=16.0°$ (c=1.0, $CHCl_3$).

[(2R)-2-bromopropyl](naphthalen-1-ylmethyl)(naphthalen-2-ylmethyl)amine((R)-3e)

$^1$H NMR ($CDCl_3$, 300 MHz) δ 1.65 (d, J=6 Hz, 3H), 2.81 (dd, J=15, 9 Hz, 1H), 2.97-3.03 (dd, J=12, 6 Hz, 1H), 3.83 (dd, J=33, 15 Hz, 4H), 4.13-4.20 (m, 1H), 7.45-7.54 (m, 4H), 7.62 (d, J=9 Hz, 2H), 7.81-7.88 (m, 8H); $^{13}$C NMR ($CDCl_3$, 300 MHz) δ 24.0 (q), 47.9 (d), 59.4 (t), 62.7 (t), 125.7 (d), 126.1 (t), 127.3 (d), 127.6 (d), 127.7 (d), 128.1 (d), 132.9 (s), 133.3 (s), 136.7 (s). $[\alpha]^{26}_D=-5.4°$ (c=1.0, $CHCl_3$).

Bis[(3-bromophenyl)methyl][(2R)-2-bromopropyl]amine((R)-3f)

$^1$H NMR ($CDCl_3$, 300 MHz) δ 1.64 (d, J=6 Hz, 3H), 2.67 (dd, J=12, 6 Hz, 1H), 2.86 (dd, J=12, 6 Hz, 1H), 3.52-3.66

(m, 4H), 4.06-4.12 (m, 1H), 7.16-7.53 (m, 8H); $^{13}$C NMR (CDCl$_3$, 300 MHz) δ 24.0 (q), 47.3 (d), 58.41 (t), 62.5 (t), 122.5 (s), 130.0 (d), 130.3 (d), 131.9 (d), 141.2 (s). $[α]^{26}_D$=+1.087° (c=1.0, CHCl$_3$).

General Procedure for Synthesis of THIQ Analogues:

To the suspension of Lewis acid catalyst (2.2 eq) in solvent (1 mL), secondary β-amino halide (1 eq) in solvent (2 mL) was added dropwise over 10~20 min at 0° C. The resulting reaction mixture was stirred at 0° C. until the reaction was complete (for the reaction of 2a, 3a, or 3f). The resulting reaction mixture was gradually warm to room temperature over 2 h and then was heated to reflux for 2 h (for reaction of 3b-3e). After completion of the reaction, the mixture was cooled to room temperature and was quenched by H$_2$O (5 mL) and then extracted with ethyl acetate (10 mL×3). The organic layer was dried over MgSO$_4$ and concentrated in vacuo to provide crude product 5 which was purified by column chromatography on silica gel (60-220 mesh) eluting with 1.5% ethyl acetate in hexanes. Enantiomeric excess was determined by chiral HPLC using the following chromatographic condition. [Column: Daicel Chiralpak® AD-H column (4.6 mm×150 mm); UV detection (λ=230 nm); Eluent: i-PrOH/Hexanes (3/97); Flow rate 1 mL/min; Temperature: 22° C.; Injection: 50 μL (1 mg of sample in 10 mL of hexanes)].

((4R)-2-benzyl-4-phenyl-1,2,3,4-tetrahydroisoquinoline ((R)-5a)

$^1$H NMR. (CDCl$_3$, 300 MHz) δ 2.70 (dd, J=9, 6 Hz, 1H), 3.10 (dd, J=9, 6 Hz, 1H), 3.70 (s, 2H), 3.77 (d, J=3 Hz, 2H), 4.28 (t, J=6 Hz, 1H), 6.92 (d, J=6 Hz, 1H), 7.07-7.33 (m, 14H); $^{13}$C NMR (CDCl$_3$, 300 MHz) δ 45.9 (d), 56.5 (t), 59.3 (t), 62.6 (t), 126.0 (d), 126.3 (d), 126.4 (d), 127.1 (d), 128.2 (d), 128.3 (d), 128.9 (d), 129.2 (d), 129.6 (d), 135.4 (s), 137.6 (s), 138.3 (s), 145.0 (s). HRMS (positive ion FAB) Calcd for C$_{22}$H$_{22}$N [M+H]$^+$ m/z 300.1747. Found: [M+H]$^+$ m/z 300.1738.

(4S)-2-benzyl-4-methyl-1,2,3,4-tetrahydroisoquinoline ((S)-5b)

$^1$H NMR (CDCl$_3$, 300 MHz) δ 1.33 (d, J=9 Hz, 3H), 2.42 (dd. J=12, 6 Hz, 1H), 2.82 (dd, J=12, 6 Hz, 1H), 3.02-3.09 (m, 1H), 3.59-3.75 (m, 4H), 7.01 (d, J=6 Hz, 1H), 7.10-7.45 (m, 8H); $^{13}$C NMR (CDCl$_3$, 300 MHz) δ21.0 (q), 33.2 (d), 56.9 (t), 58.1 (t), 62.9 (t), 125.6 (d), 126.3 (d), 126.5 (d), 127.1 (d), 127.7 (d), 128.3 (d), 129.0 (d), 134.7 (s), 138.7 (s), 139.9 (s). $[α]^{26}_D$=+25° (c=1.0, CHCl$_3$). FIRMS (positive ion FAB) Calcd for C$_{17}$H$_{20}$N [M+H]$^+$ m/z 238.1590. Found: [M+H]$^+$ m/z 238.1601.

(4R)-2,4-dibenzyl-1,2,3,4-tetrahydroisoquinoline ((R)-5c)

$^1$H NMR (CDCl$_3$, 300 MHz) δ 2.39 (d, J=12 Hz, 1H), 2.80 (d, J=12 Hz, 1H), 3.02 (t, J=12 Hz, 3H), 3.46 (d, J=15 Hz, 1H), 3.67 (dd, J=54, 12 Hz, 2H), 3.90 (d, J=15 Hz, 1H), 7.04 (d, J=6 Hz, 3H), 7.14-7.26 (m, 6H), 7.32-7.46 (m, 5H); $^{13}$C NMR (CDCl$_3$, 300 MHz) δ 41.5 (d), 42.8 (t), 53.0 (t), 56.8 (t), 63.0 (t), 125.8 (d), 126.2 (d), 126.5 (d), 127.2 (d), 128.3 (d), 128.4 (d), 128.8 (d), 129.4 (d), 135.1 (s), 138.6 (s), 138.7 (s), 141.1 (s). $[α]^{26}_D$=+ 16° (c=1.0, CHCl$_3$). HRMS (positive ion FAB) Calcd for C23H24N [M+H]$^+$ m/z 314.1903. Found: [M+H]$^+$ m/z 314.1921.

(4R)-2-benzyl-4-propyl-1,2,3,4-tetrahydroisoquinoline ((R)-5d)

$^1$H NMR (CDCl$_3$, 300 MHz) δ 0.92 (t, J=6 Hz, 3H), 1.24-1.36 (m, 3H), 1.62-1.82 (m, 1H), 2.59-2.73 (m, 2H), 2.77-2.83 (m, 1H), 3.56 (dd, J=24, 15 Hz, 2H), 3.76 (d, J=15 Hz, 2H), 7.00 (d, J=6 Hz, 1H), 7.08-7.21 (m, 3H), 7.26-7.43 (m, 5H); $^{13}$C NMR (CDCl$_3$, 300 MHz) δ 14.3 (q), 20.6 (t), 38.3 (t), 38.5 (d), 54.4 (t), 56.8 (t), 62.9 (t), 125.5 (d), 126.1 (d), 126.4 (d), 127.0 (d), 128.2 (d), 128.3 (d), 129.0 (d), 134.9 (s), 138.8 (s), 139.5 (s). FIRMS (positive ion FAB) Calcd for C19H24N [M+H]$^+$ m/z 266.1903. Found: [M+H]$^+$ m/z 266.1905. $[α]^{26}_D$=+12.7° (c=1.0, CHCl$_3$).

(4R)-4-methyl-2-(naphthalen-1-ylmethyl)-1H,2H, 3H,4H-benzo[g]isoquinoline ((R)-5e)

$^1$H NMR (CDCl$_3$, 300 MHz) δ1.57 (d, J=6 Hz, 3H), 2.66 (dd, J=12.3 Hz, 1H), 3.00 (d, J=9 Hz, 1H), 3.53-3.62 (m, 2H), 3.91 (dd, J=51, 15 Hz, 2H), 4.09 (d, J=9 Hz, 1H), 7.11 (d, J=6 Hz, 1H), 7.42-7.55 (m, 4H), 7.65 (t, J=9 Hz, 2H), 7.81-7.88 (m, 5H), 8.02 (d, J=6 Hz, 1H); $^{13}$C NMR (CDCl$_3$, 300 MHz) δ21.7 (q), 30.7 (d), 57.1 (t), 57.3 (t), 123.3 (d), 124.8 (d), 125.3 (d), 125.6 (d), 125.9 (d), 126.2 (d), 127.3 (d), 127.4 (d), 127.6 (d), 127.7 (d), 127.8 (d), 128.7 (d), 131.5 (s), 131.6 (s), 132.7 (s), 132.9 (s), 133.4 (s), 135.0 (s), 136.6 (s). $[α]^{26}_D$=+81° (c=1.0, CHCl$_3$). HRMS (positive ion FAB) Calcd for C$_{25}$H$_{24}$N [M+H]$^+$ m/z 338.1903. Found: [M+H]$^+$ m/z 338.1920.

(4R)-7-bromo-2-[(3-bromophenyl)methyl]-4-methyl-1,2,3,4-tetrahydroisoquinoline ((R)-5f)

$^1$H NMR (CDCl$_3$, 300 MHz) δ1.40 (d, J=9 Hz, 3H), 2.49 (dd, J=12, 3 Hz, 1H), 2.80 (d, J=12 Hz, 1H), 3.08-3.10 (m, 1H), 3.33 (d, J=15 Hz, 1H), 3.63 (dd, J=30, 15 Hz, 2H), 3.90 (d, J=15 Hz, 1H), 6.93-7.01 (m, 2H), 7.18-7.42 (m, 4H), 7.58 (s, 1H); $^{13}$C NMR (CDCl$_3$, 300 MHz) δ20.5 (q), 34.5 (d), 56.2 (t), 57.8 (t), 62.1 (t), 122.5 (s), 124.8 (s), 125.8 (d), 127.1 (d), 127.4 (d), 130.2 (d), 130.4 (d), 130.8 (d), 131.8 (d), 136.8 (s), 138.8 (s), 140.9 (s). FIRMS (positive ion FAB) Calcd for C17H18Br2N [M+H]$^+$ m/z 393.9801. Found: [M+H]$^+$ m/z 393.9819. $[α]^{26}_D$=+ 27° (c=1.0, CHCl$_3$).

Example 5

FIG. 6—Synthesis of Nomifensine

Synthesis of Compound 2.

To a solution of 1 (117 mg, 0.41 mmol) and PPh$_3$ (128.4 mg, 0.49 mmol) in CH$_3$CN (5 mL) at 0° C. was added NCS (65.5 mg, 0.49 mmol) portionwise at 0° C. over 20 min. The resulting mixture was stirred for 4 h while being maintained at 0° C. The ice bath was removed, and the reaction mixture was warmed to room temperature and stirred for 1 h and evaporated to dryness. The residue was purified by silica gel column chromatography eluted with 5% EtOAc in hexanes to afford 2 (73 mg, 58.4%). $^1$H NMR (CDCl$_3$, 300 MHz) δ2.27 (s, 3H), 2.94-3.12 (m, 2H), 3.90 (dd, J=21.15 Hz, 2H), 4.94 (t, J=9 Hz, 1H), 7.28-7.40 (m, 6H), 7.49-7.53 (m, 2H), 7.83 (d, J=6 Hz, 1H); $^{13}$C NMR (CDCl$_3$, 300 MHz) δ42.6 (q), 58.8 (t), 60.6 (d), 65.4 (t), 124.5 (d), 127.4 (d), 127.8 (d), 128.4 (d), 128.6 (d), 130.9 (d), 132.8 (d), 134.5 (s), 140.2 (s), 149.4 (s). $[α]^{26}_D$=+ 54.9 (c=1.0, CHCl$_3$).

Synthesis of Compound 3.

To the suspension of $AlCl_3$ (65.7 mg, 0.5 mmol) in DCE (1 mL), secondary β-amino chloride 2 (30 mg, 0.1 mmol) in DCE (2 mL) was added dropwise over 10 min at 0° C. The resulting reaction mixture was gradually warmed to room temperature while monitored by TLC. After stirring at room temperature for 5 h, the mixture was quenched by $H_2O$ (10 mL) and then extracted with ethyl acetate (10 mL×2). The organic layer was dried over $MgSO_4$ and concentrated in vacuo to provide pure product 3 (19 mg, 71%). $^1$H NMR ($CDCl_3$, 300 MHz) δ2.48 (s, 3H), 2.61 (dd, J=12, 9 Hz, 1H), 3.09 (dd, J=12.6 Hz, 1H), 3.96 (dd, J=52, 18 Hz, 2H), 4.34 (t, J=9 Hz, 1H), 7.15-7.34 (m, 7H), 7.86 (dd, J=6, 3 Hz, 1H); $^{13}$C NMR ($CDCl_3$, 300 MHz) δ46.0 (q), 46.2 (d), 55.1 (t), 60.5 (t), 122.8 (d), 126. (d), 127.0 (d), 128.4 (d), 128.7 (d), 129.0 (d), 131.2 (s), 135.2 (d), 140.7 (s), 143.8 (s), 147.7 (s). FIRMS (positive ion FAB) Calcd for $C_{16}H_{17}N_2O_2$ $[M+H]^+$ m/z 269.1285. Found: $[M+H]^+$ m/z 269.1270. $[\alpha]^{26}_D$=+11.3 (c=1.0, $CHCl_3$) (21.2% e.e.).

Synthesis of Nomifensine.

To a solution of 3 (15 mg) in ethanol (4 mL) at room temperature was added 10% Pd/C (3 mg). The reaction mixture was placed under hydrogenation apparatus set at 15 psi for 14 h. The resulting mixture was filtered via celite bed and washed thoroughly with ethanol. The filtrate was concentrated to provide pure nomifensine (100%).

Example 6

FIG. 7—Synthesis of Tryptamine Analogue R-(5)

To a solution of (S)-4b (30 mg) in dichloroethane (1 mL) cooled at −5° C. was dropwise added $AgClO_4$. The resulting mixture was stirred for 15 min at the same temperature and added to a solution of indole (50 mg) in dichloroethane (1 mL) warmed in a reaction flask. The reaction mixture was stirred for 10 h at 50° C. and treated with saturated $NH_4Cl$ (mL), and extracted with $CH_2Cl_2$. The combined organic layers were dried over $MgSO_4$, filtered, and concentrated in vacuo to the dryness. The residue was purified by silica gel (60-230 mesh) column chromatography eluted with 10% ethyl acetate in hexanes to afford 5. $[\alpha]^{26}_D$=+190.3 (c=0.1, $CHCl_3$).

Example 7

FIG. 8—Stereoselective and Regioselective Ring Opening of Aziridinium Ion by Hydride: Synthesis of Chiral Alpha Amines General Procedure for Conversion of β-Amino Alcohol to Secondary β-Amino Iodide 2.

To a solution of N,N-dialkylated alcohol 1 (0.2 mmol) and triphenyl phosphine (0.24 mmol) in $CH_2Cl_2$ (2 mL) at 0° C. was added imidazole (0.24 mmol) and iodine (0.24 mmol) portionwise over 5 min. The reaction mixture was stirred for 4 h at 0° C. and RT for 1 h after which the reaction mixture was concentrated to dryness. The residue was purified by silica gel (60-230 mesh) column chromatography eluted with 5-10% ethyl acetate in hexanes to afford pure product 2.

General Procedure for Synthesis of Chiral Alpha Amines 4.

To a solution of 3 (0.08 mmol) in $CH_3CN$ (1.25 mL) at room temperature was added $NaBH_4$ (0.16 mmol). The reaction mixture was stirred for 3 h while monitoring the reaction progress using TLC. The reaction mixture was concentrated and quenched by adding $H_2O$ (20 mL), then extracted with diethyl ether (20 mL×2). The combined organic layers were concentrated to dryness. 0.1M HCl solution (20 mL) was added to the residue and extracted with Heptane (20 mL×2) to remove byproducts. The aqueous layer was further treated with saturated $NaHCO_3$ solution and adjusted pH to 8, then extracted with diethyl ether (20 mL×2). The combined organic layers were dried over $MgSO_4$, filtered, and concentrated in vacuo to the dryness to provide the desired product 4.

Benzyl(methyl)[(2R)-1-phenylpropan-2-yl]amine ((R)-4-d)

The product (66%) was obtained as a colorless oil. $^1$H NMR ($CDCl_3$, 300 MHz) δ1.02 (d, J=7.4 Hz, 3H), 2.45-2.56 (m, 1H), 2.95-3.06 (m, 2H), 3.56-3.68 (m, 2H), 7.16-7.35 (m, 10H); $^{13}$C NMR ($CDCl_3$, 300 MHz) δ 14.0 (q), 36.9 (q), 39.4 (t), 57.8 (t), 59.8 (d), 125.8 (d), 126.8 (d), 128.2 (d), 128.7 (d), 129.3 (d), 140.1 (s), 140.8 (s). $[\alpha]^{26}_D$=−40.0 (c=1.0, $CHCl_3$).

Benzyl(ethynyl)[(2S)-1-phenylpropan-2-yl]amine ((S)-4e)

The product (60%) as a yellowish oil. $^1$H NMR ($CDCl_3$, 300 MHz) δ 0.97 (d, J=6.5 Hz, 3H), 2.16-2.42 (m, 2H), 2.43 (s, 3H), 2.91-3.07 (m, 2H), 3.44 (d, J=2.3 Hz, 2H), 7.15-7.35 (m, 5H); $^{13}$C NMR ($CDCl_3$, 300 MHz) δ 15.1 (q), 37.5 (q), 39.7 (t), 43.2 (t), 59.4 (d), 72.6 (s), 126.0 (d), 128.3 (d), 129.3 (d), 140.3 (s). $[\alpha]^{26}_D$=7.3° (c=1.0, $CHCl_3$).

benzyl(ethynyl)[(2R)-1-phenylpropan-2-yl]amine ((R)-Selegiline)

The product (55%) was obtained as a yellowish oil. $^1$H NMR ($CDCl_3$, 300 MHz) δ 0.97 (d, J=6.5 Hz, 3H), 2.16-2.42 (m, 2H), 2.43 (s, 3H), 2.91-3.07 (m, 2H), 3.44 (d, J=2.3 Hz, 2H), 7.15-7.35 (m, 5H); $^{13}$C NMR ($CDCl_3$, 300 MHz) δ 15.1 (q), 37.5 (q), 39.7 (t), 43.2 (t), 59.4 (d), 72.6 (s), 126.0 (d), 128.3 (d), 129.3 (d), 140.3 (s). $[\alpha]^{26}_D$=−7.1° (c=1.0, $CHCl_3$).

Example 8

FIG. 10—Stereoselective and Regioselective Ring Opening of Aziridinium Ion by a Grignard Reagent: Synthesis of Chiral Alpha Amines General Synthesis of Compound 4.

To a solution of (R)-3 or (S)-3 (0.1 mmol) in THF (2 mL) at 0° C. was added $AgClO_4$ (0.1 mmol). After 10 min stirring at same temperature, CuI (3 mmol) was added. Allyl magnesium bromide (1.5 mmol) was added after the reaction mixture was stirred for another 10 min. The reaction mixture was slowly warmed to room temperature. The reaction mixture was quenched with $H_2O$ (5 mL) and filtered through celite bed after stirring at room temperature for 20 h. The filtrate was extracted with $CH_2Cl_2$ (2×10 mL). The combined organic layers were dried over $MgSO_4$, filtered, and concentrated in vacuo. The residue was purified by preparative TLC using ethyl acetate/hexane=1/10 to provide pure product.

Dibenzyl[(2S)-hex-5-en-2-yl]amine((S)-4a)

Pure product (S)-3b (11 mg, 44%) was isolated from prep-TLC. $^1$H NMR ($CDCl_3$, 300 MHz) δ 1.03 (d, J=6.6 Hz, 3H), 1.28-1.38 (m, 1H), 1.68-1.76 (m, 1H), 1.97-2.05 (m, 1H), 2.17-2.22 (m, 1H), 2.71-2.78 (m, 1H), 3.43 (d, J=13.8 Hz, 2H), 3.73 (d, J=13.8 Hz, 2H), 4.85-4.96 (m, 2H), 5.68-5.79 (m, 1H), 7.19-7.40 (m, 10H); $^{13}$C NMR (CDCl$_3$, 300 MHz) δ 13.3 (q), 31.2 (t), 33.3 (t), 52.2 (d), 53.4 (t), 114.1 (t), 126.6 (d), 128.1 (d), 128.7 (d), 139.1 (s), 140.7 (s). $[\alpha]^{26}_D$=+ 14.5° (c=0.6, CHCl$_3$).

Example 9

FIGS. 11 and 12—Stereoselective and Regioselective Ring Opening of Aziridinium Ions by Sodium Diethyl Malonate: Synthesis of Gamma Butyric Acid (GABA) Analogue General Method for Preparation of Compound 5.

To a solution of compound 2 or 3 (0.09 mmol) in CH$_3$CN (1 mL) at room temperature was added sodium diethyl malonic ester (0.18 mmol). The reaction mixture was stirred for 3 min and monitored by TLC. The reaction mixture was concentrated to dryness and treated with Et$_2$O (5 mL) and filtered to remove the excess sodium diethyl malonic ester. The filtrate was concentrated in vacuo to provide pure product 5.

1,3-dimethyl 2-[(1R)-2-(dibenzylamino)-1-phenyl-ethyl]propanedioate((R)-5a)

Pure product (R)-5a (37.8 mg, 100%) was obtained. $^1$H NMR (CDCl$_3$, 300 MHz) δ2.63-3.69 (m, 1H), 2.74-2.81 (m, 1H), 3.34-3.38 (m, 5H), 3.62 (d, J=10.1 Hz, 1H), 3.75-3.82 (m, 6H), 7.04-7.12 (m, 6H), 7.15-7.26 (m, 9H); $^{13}$C NMR (CDCl$_3$, 300 MHz) δ 43.8 (d), 52.2 (q), 52.6 (q), 56.5 (d), 57.3 (t), 58.3 (t), 126.8 (d), 126.9 (d), 128.1 (d), 128.7 (d), 128.9 (d), 139.0 (s), 139.9 (s), 168.1 (s), 168.8 (s). $[\alpha]^{26}_D$=-4.3° (c=1.0, CHCl$_3$).
Synthesis of Compound 6.

Compound (R)-5a was dissolved in the mixture of acetic acid (30 mL) and conc. HCl (100 mL), and the resulting solution was maintained under reflux for 24 h. The reaction was allowed to room temperature, and the resulting precipitate was filtered while washing with isopropanol and dried in vacuo to provide pure 6. The volume of the filtrate was reduced to half and left in the freezer, and the product was filtered and obtained as white solid formed.
Synthesis of Phenibut.

To a solution of 6 in ethanol (4 mL) at room temperature was added 10% Pd/C (3 mg) under Ar (g). The reaction mixture was placed under hydrogenation apparatus for 14 h. The resulting mixture was filtered via Celite bed and washed thoroughly with ethanol. The filtrate was concentrated to provide (R)-Phenibut.

Example 10

FIG. 13—Stereoselective and Regioselective Ring Opening of Aziridinium Ions Via Intramolecular Rearrangement: Synthesis of Oxomorpholines General Procedure for Synthesis of Substituted Oxomorpholine Analogues.

To a solution of a substituted β-amino bromide (0.14 mmol) in CH$_3$CN (5 mL) was added DIPEA (0.42 mmol), and the reaction mixture was allowed to reflux until the reaction was complete. The reaction mixture was concentrated, and the residue was purified via column chromatography on silica gel (60-230 mesh) column chromatography eluted with 30% ethyl acetate in hexanes to afford the product.

tert-butyl 2-[(2R)-2-methyl-6-oxomorpholin-4-yl]acetate((R)-3a)

The reaction mixture was heated for 2 days. (R)-3a (24 mg, 77%) was obtained as a colorless oil. $^1$H NMR (CDCl$_3$, 300 MHz) δ1.34 (d, J=6.4 Hz, 3H), 1.45 (s, 9H), 2.52 (dd, J=9.4, 1.5 Hz, 1H), 2.99 (dd, J=4.7, 3.8 Hz, 1H), 3.19 (s, 2H), 3.29 (d, J=8.7 Hz, 1H), 3.64 (d, J=7.9 Hz, 1H), 4.62-4.67 (m, 1H); $^{13}$C NMR (CDCl$_3$, 300 MHz) δ 19.0 (q), 28.1 (q), 53.8 (t), 54.7 (t), 57.6 (t), 76.0 (d), 82.0 (s), 167.7 (s), 168.8 (s). $[\alpha]^{26}_D$=-5.7° (c=1.0, CHCl$_3$).

tert-butyl 2-[(2R)-2-benzyl-6-oxomorpholin-4-yl]acetate((R)-3b)

The reaction mixture was heated for 4 days. (R)-3b (41.4 mg, 50%) was obtained as a colorless oil. $^1$H NMR (CDCl$_3$, 300 MHz) δ 1.44 (s, 9H), 2.60 (dd, J=8.7, 1.8 Hz, 1H), 2.87-2.97 (m, 2H), 3.07-3.14 (m, 1H), 3.18 (s, 2H), 3.36 (d, J=8.7 Hz, 1H), 3.66 (d, J=9.3 Hz, 1H), 4.70-4.75 (m, 1H), 7.20-7.35 (m, 5H); $^{13}$C NMR (CDCl$_3$, 300 MHz) δ 28.1 (q), 39.7 (t), 52.2 (t), 54.0 (t), 57.7 (t), 80.0 (d), 82.0 (s), 127.0 (d), 128.7 (d), 129.4 (d), 135.9 (s), 167.5 (s), 168.7 (s). $[\alpha]^{26}_D$=+5.0° (c=1.0, CHCl$_3$)

tert-butyl 2-[(6R)-2-oxo-6-(propan-2-yl)morpholin-4-yl]acetate((R)-3c)

The reaction mixture was heated for 5 d. (R)-3c (10.1 mg, 35%) was obtained as an colorless oil. $^1$H NMR (CDCl$_3$, 300 MHz) δ 0.97 (d, J=6.8 Hz, 3H), 1.03 (d, J=6.8 Hz, 3H), 1.47 (s, 9H), 1.87-1.94 (m, 1H), 2.57-2.64 (m, 1H), 2.96-3.02 (m, 1H), 3.22 (s, 2H), 3.26-3.32 (m, 1H), 3.65-3.71 (m, 1H), 4.24-4.31 (m, 1H); $^{13}$C NMR (CDCl$_3$, 300 MHz) δ17.9 (q), 18.1 (q), 28.1 (q), 31.2 (d), 51.1 (t), 54.0 (t), 57.9 (t), 82.0 (s), 84.3 (d), 167.9 (s), 168.8 (s). $[\alpha]^{26}_D$=8.7 (c=0.5, CHCl$_3$).

Example 11

FIG. 14—Stereoselective and Regioselective Substitution Reactions of Aziridinium Ions Experimental tert-butyl 2-{([2-(tert-butoxy)-2-oxoethyl][(2S)-1-(diethylamino)-3-phenylpropan-2-yl]amino}acetate ((S)-3)

To a stirred solution of (R)-1b (200 mg, 0.46 mmol) in solvent CH$_3$CN (2 mL) was added diethylamine (99.3 mg, 1.37 mmol). The reaction mixture was stirred at room temperature for 1d, concentrated, and the residue was purified via silica gel (60-220 mesh) column chromatography eluting with 10% methanol in CH$_2$Cl$_2$ to provide the pure (S)-3 (150 mg, 75%) as a colorless oil. $^1$H NMR (CDCl$_3$, 300 MHz) δ 0.90 (t, J=7.1 Hz, 6H), 1.44 (s, 18H), 2.24-2.30 (m, 1-1), 2.42-2.50 (m, 4H), 2.54-2.61 (m, 1H), 2.65-2.85 (m, 2H), 3.13-3.19 (m, 1H), 3.41-3.55 (m, 4H), 7.13-7.27 (m, 5H); $^{13}$C NMR (CDCl$_3$, 300 MHz) δ 11.6 (q), 28.1 (q), 37.6 (t), 47.1 (t), 53.8 (t), 54.7 (t), 62.2 (d), 80.5 (s), 125.7 (d), 128.1 (d), 129.3 (d), 140.8 (s), 171.5 (s). HRMS (positive ion FAB) Calcd for C$_{25}$H$_{43}$N$_2$O$_4$ [M+H]$^+$ m/z 435.3217. Found: [M+H]⁺ m/z 435.3237. $[\alpha]^{26}_D$=−16.6° (c=1.0, CHCl₃). Chiral-HPLC was performed on Agilent 1200 (Agilent, Santa Clara, Calif.) equipped with a detector (λ=254 nm), a thermostat set at 35° C. and a Chiralpak® AD-H (4.6×150 mm, Chiral Technologies Inc., West Chester, Pa.). The mobile phase of a binary gradient (0-100% B/40 min; solvent A=Hexanes; solvent B=i-PrOH) was used. $t_R$=(S)-enantiomer: 17 min (100% ee). Synthesis procedures and NMR data of (R)-3 are identical to (S)-3. $t_R$=(R)-enantiomer: 20 min (100% ee)

Synthesis of (S)-3 from (R)-1b

To a stirred solution of (R)-1b (50.0 mg, 0.11 mmol) in CH₃CN (1.5 mL) was added silver perchlorate (117 mg, 0.57 mmol), and the reaction mixture was stirred at −10° C. for 25 min. After which, diethylamine (24.8 mg, 0.34 mmol) was added dropwise and the resulting mixture was stirred at room temperature for 1 h. The resulting mixture was filtered and concentrated in vacuum. The residue was treated with H₂O (10 mL) and 5 drops of 2M aqueous NaOH and then extracted with CH₂Cl₂ (10 mL×3). The combined organic layer was treated with MgSO₄ and concentrated under vacuum. The same work-up was done two more times and pure (S)-3 (45.3 mg, 92%) was obtained as a colorless oil after the work-up.

$[\alpha]^{26}_D$=16.4 (c=1.0, CHCl₃).

tert-butyl 2-{[2-(tert-butoxy)-2-oxoethyl][(2S)-1-{[(1R,2R)-2-hydroxy-2,3-dihydro-1H-inden-1-yl]amino}-3-phenylpropan-2-yl]amino}acetate((S)-6)

To a stirred solution of (R)-1b (50 mg, 0.11 mmol) in CH₃CN (2.0 mL) was added silver perchlorate (117 mg, 0.57 mmol), and the reaction mixture was stirred at −10° C. for 30 min. After which, 5 (50.6 mg, 0.34 mmol) was added portionwise and the resulting mixture was stirred at room temperature for 7 h. The resulting mixture was filtered and concentrated in vacuo. The residue was treated with H₂O (10 mL) and 2M aqueous NaOH (1 mL) and then extracted with CH₂Cl₂ (15 mL×3). The combined organic layer was treated with MgSO₄ and concentrated under vacuum. The same work-up was done two more times and pure (S)-6 (51 mg, 88%) was got as a colorless oil. ¹H NMR (CDCl₃, 300 MHz) δ 1.46 (s, 18H), 2.45 (dd, J=9.5, 1.9 Hz, 4H), 2.57-3.04 (m, 7H), 3.13-3.24 (m, 3H), 3.32-3.50 (m, 5H), 3.98-4.01 (m, 1H), 4.27-4.33 (m, 1H), 7.14-7.30 (m, 9H); ¹³C NMR (CDCl₃, 300 MHz) δ 28.1 (q), 36.5 (t), 38.6 (t), 48.1 (t), 53.8 (t), 65.2 (d), 70.5 (d), 78.2 (d), 81.4 (s), 124.3 (d), 124.9 (d), 126.3 (d), 126.7 (d), 127.6 (d), 128.5 (d), 128.6 (d), 129.1 (d), 129.3 (d), 139.2 (s), 139.7 (s), 142.3 (s), 171.8 (s).

tert-butyl 2-{[2-(tert-butoxy)-2-oxoethyl][(2R)-1-cyano-3-phenylpropan-2-yl]amino}acetate((R)-4)

To the stirred solution of (S)-1b (50 mg, 0.11 mmol) in DMSO (2 mL) was added NaCN (7 mg, 0.14 mmol). The reaction mixture was stirred at room temperature for 14 h. The resulting mixture was treated with H₂O (25 mL) and extracted with ethyl acetate (25 mL×3). The combined organic layer was treated with MgSO₄ and concentrated under vacuum. The reaction mixture was purified by column chromatography eluted with 8% Ethyl acetate in hexanes to afford (R)-4 (26 mg, 61%) was obtained as a yellow oil. ¹H NMR (CDCl₃, 300 MHz) δ 1.47 (s, 18H), 2.39-2.58 (m, 2H), 2.78 (dd, J=15.12 Hz, 1H), 3.11-3.17 (m, 1H), 3.33-3.38 (m, 1H), 3.57 (dd, J=33.18 Hz, 4H), 7.22-7.33 (m, 5H); ¹³C NMR (CDCl₃, 300 MHz) δ 21.0 (t), 28.1 (q), 38.6 (t), 53.6 (t), 61.3 (d), 81.3 (s), 118.7 (s), 126.8 (d), 128.7 (d), 129.0 (d), 138.0 (s), 171.0 (s). $[\alpha]^{26}_D$=−9.9° (c=1.6, CH₃Cl).

tert-butyl 2-{[2-(tert-butoxy)-2-oxoethyl][(2S)-1-cyano-3-phenylpropan-2-yl]amino}acetate((S)-4)

To the stirred solution of (R)-1b (50 mg, 0.11 mmol) in DMSO (2 mL) was added NaCN (7 mg, 0.14 mmol). The reaction mixture was stirred at room temperature for 14 h. The resulting mixture was treated with H₂O (25 mL) and extracted with ethyl acetate (25 mL×3). The combined organic layer was treated with MgSO₄ and concentrated under vacuum. The reaction mixture was purified by preparative TLC eluted with 25% Ethyl acetate in hexanes to afford (S)-4 (32.7 mg, 77%) was obtained as a yellow oil. NMR is identical to (R)-4. $[\alpha]^{26}_D$=9.3° (c=1.0, CH₃Cl)

Example 12

FIG. 15—Stereoselective and Regioselective Nucleophilic Substitution Reaction of Aziridinium Ion General Synthesis of Compound 5.

To the stirred solution of (R)-3a (0.1 mmol) in CH₃CN (1.25 mL) and/or H₂O (0.25 mL) was added nucleophile (0.11 mmol). The reaction mixture was stirred at room temperature. When the reaction was complete, the mixture was treated with H₂O (25 mL) and extracted with ethyl acetate (25 mL×3). The combined organic layer was treated with MgSO₄ and concentrated in vacuo.

Synthesis of Compound (R)-5c.

To the stirred solution of (R)-3a (0.1 mmol) in CH₃CN (1.25 mL) was added tetrabutyl ammonium fluoride (TBAF, 0.11 mmol). The reaction mixture was stirred at room temperature for 1 min. Pure 4c was obtained (100%). $[\alpha]^{26}_D$=−12.3° (c=1.0, CHCl₃).

Example 13

FIG. 16—Stereoselective and Regioselective Ring Opening of Aziridinium Ions: Convenient One-Pot Reaction of Enantiomerically Enriched Amines with Functionality General Synthesis of Compound 4.

To a solution of 1 (0.4 mmol) and PPh₃ (0.48 mmol) in CH₃CN (5 mL) at 0° C. was added NBS (0.48 mmol) over 5 min. The resulting mixture was stirred for 4 h while being maintained at 0° C. The ice bath was removed, and the reaction mixture was warmed to room temperature and stirred for 1 h. Nucleophilic reagent (0.48 mmol) was added to the reaction mixture followed by the addition of H₂O (0.5 mL). The reaction mixture was allowed to stir at RT for 1 h. The residue was purified via column chromatography on silica gel (60-230 mesh) eluting with 15% EtOAc in hexanes to afford the desired nucleophilic addition product.

(3S)-3-(dibenzylamino)butanenitrile (4b)

Pure 4b (80 mg, 77%) was obtained as a white solid. ¹H NMR (CDCl₃, 300 MHz) δ 1.20 (d, J=6 Hz, 3H), 2.31-2.39 (m, 1H), 2.51-2.59 (m, 1H), 2.23-2.25 (m, 1H), 3.61 (dd, J=45, 15 Hz, 4H), 7.22-7.43 (m, 10H); ¹³C NMR (CDCl₃, 300 MHz) δ 14.0 (q), 21.9 (t), 50.5 (d), 53.5 (t), 118.7 (s), 127.21 (d), 128.4 (d), 128.6 (d), 139.1 (s). $[\alpha]^{26}_D$=3.1° (c=1.0, CHCl₃).

Thus, the invention provides stereoselective and regioselective synthesis of compounds via nucleophilic ring opening reactions of aziridinium ions, such as prepared from β-amino alcohols. The method of this invention provides efficient synthesis, often with reduced reaction steps and high stereoselectivity and regioselectivity, for both new compounds and important key precursor molecules to commercially available drug compounds.

The invention illustratively disclosed herein suitably may be practiced in the absence of any element, part, step, component, or ingredient which is not specifically disclosed herein.

While in the foregoing detailed description this invention has been described in relation to certain preferred embodiments thereof, and many details have been set forth for purposes of illustration, it will be apparent to those skilled in the art that the invention is susceptible to additional embodiments and that certain of the details described herein can be varied considerably without departing from the basic principles of the invention.

The invention claimed is:

1. A method of stereoselective or regioselective synthesis through ring opening of aziridinium ions, comprising:
   converting a substituted β amino alcohol to a substituted alkylating agent, wherein the substituted alkylating agent is a substituted β-amino halide comprising:

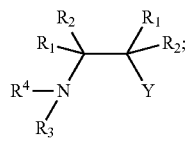

converting the substituted alkylating agent in the presence of halosequestering agent comprising $AgClO_4$, $AgOTf$, $Ag_2CO_3$, $AgOTs$, $AgNO_3$, $AgSbF_6$, or $AgBF_4$ to a substituted aziridinium ion selected from:

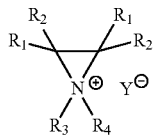

where: Y is a non-nucleophilic counter anion or a leaving group comprising halide, perchlorate, tetrafluoroborate, hexafluoroantimonate, mesylate, triflate, carbonate, nitrate, phthalimide, or succinimide; each of $R_{1-4}$ independently is hydrogen, carboxyalkyl, alkylamido, alkyl, allyl, benzyl, benzyloxyalkyl, cycloalkyl, heterocyclyl, alkoxy, hydroxyalkyl, aryl, $CH_2Ar$, aryloxy, hydroxyaryl, heteroaryl, phenyl, vinyl, alkynyl, alkenyl, substituted carbonyl, halo, haloalkyl, nitrile, oxo, substituted oxo, substituted silyl, thiol, benzhydryl, silyl, substituted carboxyl, aminoalkyl, alkoxycarbonyl, alkylamido, furannylalkyl, alkylthioalkyl, arylhydroxyalkyl, indanyl, indolylalkyl, naphthylalkyl, imidazolylalkyl, pyridiylalkyl, phthalimidyl, maleimidyl, benzothiophenylalkyl, thiophenylalkyl, thioalkyl, thioaryl, thiobenzyl, hydroxy, tosyl, nosyl, a protected amine, carboxyl, carboxyalkyloxy, amino, carboxylic acid, haloalkylamido, aldehyde, alkylamino, amido, trityl, tert-butyloxycarbonyl, carbobenzyloxy, acetyl, dimethoxybenzyl, p-methoxybenzyl, any two vicinal carbons of $R_1$ and $R_2$ together form a fused ring, any two geminal carbons, $R_1$ and $R_2$ are bonded together and form a spiro ring, any of $R_{1-4}$ is attached to chiral carbon, or is one of:

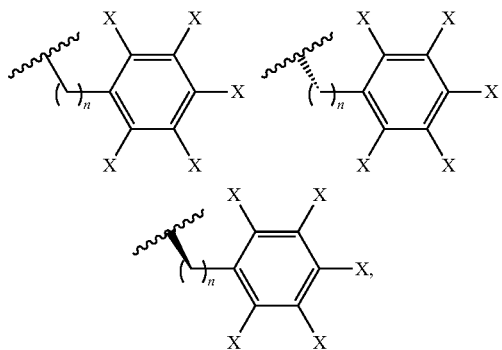

where n=1-10 and X is hydrogen, halo, cyano, alkyl, aryl, hydroxyl, nitro, amino, alkylamino, dialkylamino, substituted amine, substituted carbonyl, isocyanate, cyanate ester, protected amine, protected hydroxyl, protected carboxyl, boronic acid, borinic acid, borinate ester, triflate, silyl, substituted silyl, thiocyano, isothiocyano, alkoxy, aryloxy, carboxyl, carboxylic acid, carboxyalkyl, carboxyalkyloxy, ester, amido, aldehydo, alkylamido, or haloalkylamido, and/or $R_3$ or $R_4$ can also be selected from:

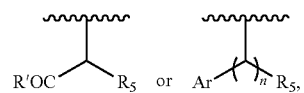

where n=1-3 and Ar is an aromatic ring bonded to one of the n carbons; $R_5$ is as defined for $R_1$-$R_4$; R' independently is OH, $NH_2$, $NR''_2$, or OR'', wherein R'' independently is alkyl, tert-butyl, allyl, benzyl, $CH_2Ar$, silyl, trityl, an amine protecting group, a carboxyl protecting group, or a hydroxyl protecting group; and wherein Ar in $CH_2Ar$ represents an aromatic rind; and stereoselectively or regioselectively reacting the aziridinium ion in situ with a nucleophile in a nucleophilic ring opening reaction to obtain a compound, wherein the compound comprises one of:

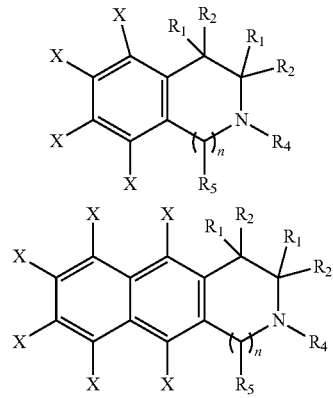

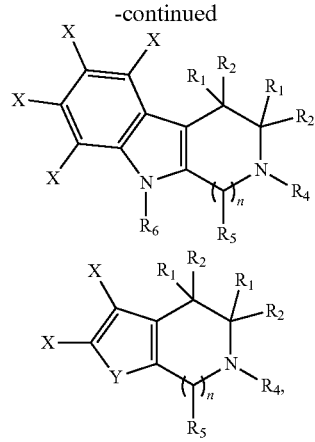

where: n=1, 2, or 3; Y=O, NH, or S; each of each of $R_{1-5}$ and X are as defined above, and $R_6$ is as defined for $R_{1-5}$.

2. The method of claim 1, further comprising stereoselectively or regioselectively reacting the aziridinium ion in the presence of a catalyst.

3. The method of claim 2, wherein the catalyst comprises a Lewis acid, an organocatalyst, or combinations thereof.

4. The method of claim 1, wherein the synthesis occurs without isolation of any intermediate compound.

\* \* \* \* \*